United States Patent
Hooker et al.

(10) Patent No.: US 10,896,405 B1
(45) Date of Patent: Jan. 19, 2021

(54) SYSTEMS AND METHODS RELATING TO HEALTH POLICY COVERAGE OF MEDICAL PRODUCTS AND SERVICES

(71) Applicant: Concert Genetics, Inc., Franklin, TN (US)

(72) Inventors: Gillian W. Hooker, Brentwood, TN (US); Blake S. Blackshear, Franklin, TN (US); Robert L. Metcalf, Nashville, TN (US); Marshall Cottrell, Franklin, TN (US); Taylor Murphy, Franklin, TN (US)

(73) Assignee: Concert Genetics, Inc., Franklin, TN (US)

( * ) Notice: Subject to any disclaimer, the term of this patent is extended or adjusted under 35 U.S.C. 154(b) by 0 days.

(21) Appl. No.: 16/808,612

(22) Filed: Mar. 4, 2020

Related U.S. Application Data

(60) Provisional application No. 62/813,557, filed on Mar. 4, 2019.

(51) Int. Cl.

| | |
|---|---|
| *G06Q 10/10* | (2012.01) |
| *G06Q 40/08* | (2012.01) |
| *G06N 20/00* | (2019.01) |
| *G16H 10/40* | (2018.01) |
| *G16H 10/20* | (2018.01) |
| *G16H 70/20* | (2018.01) |

(52) U.S. Cl.
CPC ............ *G06Q 10/10* (2013.01); *G06N 20/00* (2019.01); *G06Q 40/08* (2013.01); *G16H 10/20* (2018.01); *G16H 10/40* (2018.01); *G16H 70/20* (2018.01)

(58) Field of Classification Search
None
See application file for complete search history.

(56) References Cited

U.S. PATENT DOCUMENTS

| | | | |
|---|---|---|---|
| 2009/0144088 A1* | 6/2009 | Zubiller | G06Q 20/102 705/3 |
| 2020/0126137 A1* | 4/2020 | Pilkington | G06N 20/00 |

OTHER PUBLICATIONS

Rubinstein et al., The NIH genetic testing registry: a new, centralized database of genetic tests to enable access to comprehensive information and improve transparency, Nov. 27, 2012, Nucleic Acids Research, 20136, vol. 41, D925-D935, doi:10.1093/nar/gks1173 (Year: 2012).*

* cited by examiner

*Primary Examiner* — Devin C Hein
(74) *Attorney, Agent, or Firm* — Meunier Carlin & Curfman LLC

(57) ABSTRACT

The present disclosure, in one aspect, relates to implementing coverage outcome algorithms (COAs) to determine a coverage outcome indicating whether a medical service or product is covered by a health policy, and outputting the coverage outcome. In some embodiments, the COAs each utilize triggers associated with the medical service or product and/or coverage criteria associated with the health policy.

20 Claims, 21 Drawing Sheets
(15 of 21 Drawing Sheet(s) Filed in Color)

SYSTEMS AND METHODS RELATING TO HEALTH POLICY COVERAGE OF MEDICAL PRODUCTS AND SERVICES

CROSS-REFERENCE TO RELATED PATENT APPLICATION

This application claims priority to and the benefit of U.S. Provisional Patent Application No. 62/813,557, filed Mar. 4, 2019, the entire contents of which is hereby incorporated by reference.

BACKGROUND

The present disclosure generally relates to medical products and services such as genetic testing products and services. Laboratories are producing an increasing number of medically related tests, and each laboratory provides different information about their specific tests. There is an efficiency loss resulting in higher health care costs and the increased possibility of fraud, waste, and abuse surrounding diagnostics. Inherent within the healthcare system, there are also a variety of mechanisms that require information about medical products and services to be structured and applied. It is with respect to these and other considerations that the various embodiments described below are presented.

SUMMARY

Some aspects of the present disclosure relate to health plans and policies, and to determining whether a policy covers particular medical products or services, for example genetic testing related products or services. A health plan policy (sometimes referred to herein as "health policy" or "policy") can be considered to be a compilation of the medical requirements and billing requirements for a provider to receive reimbursement. In some embodiments, a health plan policy is a health insurance policy. In some embodiments, health plan policies are broken down into discrete elements that can be aligned with a particular taxonomy, with a process for creating, storing, and updating the discrete elements, and in some embodiments, the present disclosure relates to utilizing a combined representation (e.g., GTU, category, policy) in an automated process for reviewing claims for eligibility, payment, fraud, waste, and/or abuse, and for enabling the ordering of tests in a provider's workflow. Among other advantages and benefits provided by certain embodiments of the present disclosure, coverage outcome algorithms (COAs) can be utilized to address the variability in the market with regard to how health plans can structure policies.

In some aspects, the present disclosure relates to a method which, in some embodiments, includes: determining, based at least on implementing one or more coverage outcome algorithms (COAs), a coverage outcome indicating whether a medical service or product (e.g., a genetic testing service or product) is covered by a health policy; and outputting the coverage outcome. The COAs can each utilize triggers associated with the medical service or product and/or coverage criteria associated with the health policy.

In some embodiments, the triggers correspond to one or more identifiers for the medical service or product. In some embodiments, the identifier(s) for the medical service or product are determined at least in part using a trainable machine learning model. The identifiers can include a genetic testing unit (GTU) and/or a categorical bin associated with the medical service or product. The identifier(s) can correspond to a claim for coverage for the medical service or product.

Implementing the one or more COAs can include generating, based on the coverage criteria associated with the medical service or product, a plurality of questions prompting a user for information associated with the medical service or product and/or the health policy. The coverage outcome can be determined at least in part on responses provided by the user in response to the plurality of questions.

In some embodiments, prompting the user for the information and receiving the responses provided by the user are performed through an interactive user interface. Generating the plurality of questions can include customizing at least some of the questions according to the identity of the user as a patient, health care provider, or health policy representative.

In some embodiments, the method also includes determining, based on at least one of the triggers, whether there is a predetermined coverage outcome corresponding to the medical service or product and, responsive to determining that there is a predetermined coverage outcome, outputting the predetermined coverage outcome.

In another aspect, the present disclosure relates to a system which, in some embodiments, includes: one or more processors; and a memory device coupled to the one or more processors, wherein the memory device stores instructions that, when executed by the one or more processors, cause the system to perform functions that include: determining, based at least on implementing one or more coverage outcome algorithms (COAs), a coverage outcome indicating whether a medical service or product is covered by the health policy; and outputting the coverage outcome, wherein the COAs each utilize at least one of: triggers associated with the medical service or product; and coverage associated with the health policy.

In some embodiments, the medical service or product is a genetic testing service or product.

In some embodiments, the memory device stores further instructions that, when executed by the one or more processors, cause the system to determine the one or more identifiers for the medical service or product at least in part using a trainable machine learning model.

In some embodiments, the triggers correspond to one or more identifiers for the medical service or product. In some embodiments, the one or more identifiers comprise at least one of a genetic testing unit (GTU) and a categorical bin associated with the medical service or product. In some embodiments, the one or more identifiers correspond to a claim for coverage by the health policy for the medical service or product.

In some embodiments, the system also includes an interactive user interface coupled to the one or more processors, and implementing the one or more COAs includes generating, based on the coverage criteria associated with the medical service or product, a plurality of questions prompting a user for information associated with the selected medical service or product and/or the health policy. The coverage outcome can be determined at least in part on responses provided by the user, through the interactive user interface, in response to the plurality of questions. Generating the plurality of questions comprises customizing at least some of the questions according to the identity of the user as a patient, health care provider, or health policy representative.

In some embodiments, the memory device stores further instructions that, when executed by the one or more processors, cause the system to: determine, based on at least one of the triggers, whether there is a predetermined coverage outcome corresponding to the medical service or product; and responsive to determining that there is a predetermined coverage outcome, output the predetermined coverage outcome.

In yet another aspect, the present disclosure relates to a non-transitory computer-readable medium storing instructions that, when executed by one or more processors, cause one or more computing devices to perform functions that include determining, based at least on implementing one or more coverage outcome algorithms (COAs), a coverage outcome indicating whether a medical service or product is covered by the health policy. The functions performed also include outputting the coverage outcome. The COAs can each utilize at least one of: triggers associated with the medical service or product; and coverage criteria associated with the health policy.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with the color drawing(s) will be provided by the Office upon request and payment of the necessary fee.

FIGS. 2A and 2B are screen shots illustrating various aspects relating to "Diff" associated with testing products, in accordance with some embodiments of the present disclosure.

FIGS. 10-13 are screen shots relating to a graphical user interface for performing various aspects relating to health plan policies in accordance with some embodiments of the present disclosure.

FIGS. 14A-14F are screen shots relating to a graphical user interface for functions relating to determining coverage by a health plan policy in accordance with some embodiments of the present disclosure.

DETAILED DESCRIPTION

Figure 1:
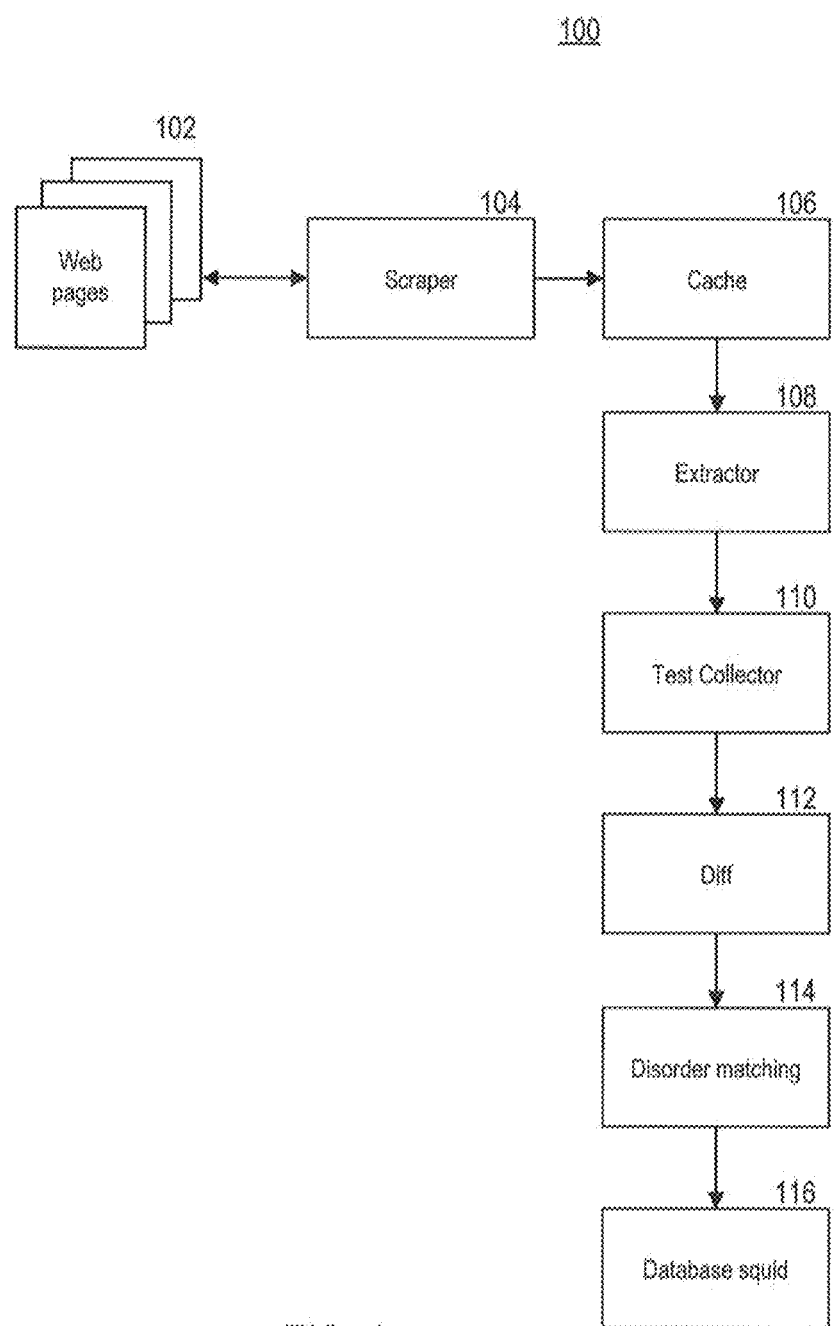
FIG. 1 is a diagram of a system and processes for performing certain aspects of tracking, monitoring, and standardizing molecular and diagnostic testing products and services in accordance with some embodiments of the present disclosure.

Although example embodiments of the present disclosure are explained in detail, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Moreover, titles or subtitles may be used in this specification for the convenience of a reader, which shall have no influence on the scope of the present disclosure.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. In describing embodiments, terminology related to laboratory products can be used interchangeably. For example, genetic testing products, laboratory testing products, testing products, or the like do not necessarily indicate different products/tests/etc.

It is to be understood that the mention of one or more steps of a method does not preclude the presence of additional method steps or intervening method steps between those steps expressly identified. Steps of a method may be performed in a different order than those described herein. Similarly, it is also to be understood that the mention of one or more components in a device or system does not preclude the presence of additional components or intervening components between those components expressly identified.

In the following detailed description, references are made to the accompanying drawings that form a part hereof and that show, by way of illustration, specific embodiments or examples. In referring to the drawings, like numerals represent like elements throughout the several figures.

In some embodiments, supervised and/or unsupervised machine learning can be used. For example, when a specific genetic test is changed by a laboratory or test provider (e.g., a change in the scope of target genes), machine learning can be used to improve the efficacy of rematching that test with its associated product and "Bin", allowing the system to learn to better identify the product and/or bin based on underlying patterns or features. A Bin as described herein may also be referred to as a category.

Examples of machine learning processes and algorithms that may be utilized in performing certain aspects of the present disclosure include, but are not limited to, random force, support vector machines (SVM), random forest, neural networks, nearest-neighbor, Naïve Bayes, AdaBoost, QDA, decision trees, Gaussian processes, k-means, DBSCAN, and affinity propagation. For example, some examples of machine learning models employed in various embodiments include, but are not limited to, XGBoost, naïve Bayes, support vector machines, Deep Learning using various architectures such as LSTM, and random forests.

Now referring to the system and processes (collectively labeled 100) illustrated in FIG. 1, according to some embodiments, a scraper 104 such as a web scraper can be used to obtain data from laboratory and testing company websites 102 which contain information regarding testing products and/or services such as genetic testing products and services. In some embodiments, the data is in HTML and can then be stored as raw HTML in a cache 106. The scraper 104 may be an autonomous agent, for example, and may be scheduled to scrape HTML or desired data from the various websites according to a schedule that may be customized for the respective sites, or otherwise run periodically to ensure that up-to-date product and service information is obtained.

An extractor/standardizer 108 (hereinafter generally referred to as an extractor) can automatically pull data from the cache 106, such as the raw HTML data, and produce structured data. The structured data may be formed into various standardized fields relating to the testing products and services, for charts and/or tables to be displayed to and manipulated by a user, as will be later described with reference to, for instance, embodiments relating to a database "squid" 116 and "Diff" 112. In some embodiments, the structured data may be a JSON object. The extractor can be a rules-based data extraction tool (e.g., using javascript-based rules). In some embodiments, the standardized fields produced by the extractor represent specific information about the testing products. The testing product-specific information can be used to analyze and sort the specific testing products. For example, standardized fields can include target gene(s), target analyte(s), testing technique, testing methodology, specific diseases, and/or specific conditions, as will be further described below and shown in additional Figures.

Figure 4:
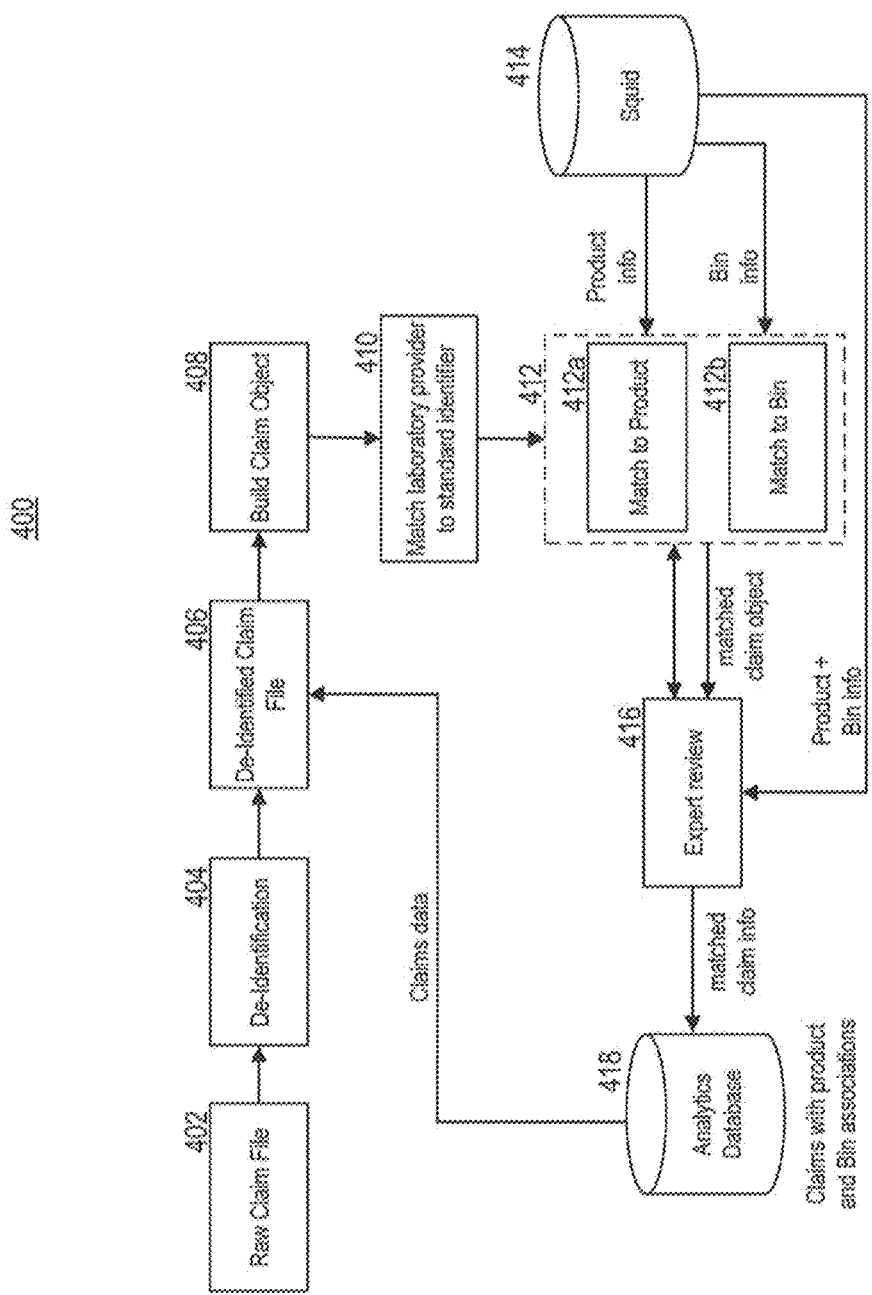
FIG. 4 illustrates a system and process for matching a claim to a product and/or Bin, in accordance with some embodiments of the present disclosure.

In some embodiments, a database (not shown) contains information used to standardize information about individual laboratory companies. This includes, or may include, information relevant to the location of the laboratory, certifications, location, contact information, NPIs, EINs, personnel, and other relevant information used to determine and standardize a particular laboratory business entity as it exists. In some embodiments, this information may be used by a variety of different components of this process such as 108 (FIG. 1) and 410 (FIG. 4).

In some embodiments, a database (not shown) can be used during the standardization by the extractor 108. The database can contain a library of terms used to standardize the information. For example, a consortium may have standard terms that represent specific gene(s) targeted by the testing product. The consortium's standard terms can be utilized to standardize the cached HTML information, thus presenting a uniform set of information across multiple tests from multiple laboratories.

In some embodiments, the extractor 108 can be used for, or in connection with, processes for Genetic Testing Unit (GTU) assignment. According to some embodiments, testing products can be assigned a GTU. One of the many challenges for laboratories, hospitals, clinicians, and payers is that there are no consistent identifiers for products across the industry. GTUs can allow for versioning and tracking individual testing products through time, i.e., GTUs can be used to track a specific product as it evolves over time. A GTU is based on the concept of an orderable unit and can be standardized down to the specific methodology of that orderable unit. As products evolve, the GTU is designed to take into consideration these various factors. It can be versioned, traceable through time, and relatable to specific marketing material specified on a laboratory's website. Thus, it is an individual record of the most specific type of actionable testing within the marketplace. GTUs can also be designed to be able to translate between various identifiers used within the healthcare system. Currently, products, and thus GTUs, can have associated CPT codes that are specified by the laboratories with these products. UDIs and Z-codes can be associated as necessary. A GTU can be stored in a database as a GUID and versioned using the ISO 8601 standard. The GTU and its version is a unique representation of a test's attributes, including its Bin. In some embodiments, the version (timestamp) is updated when any data associated with the test changes. Minor changes, such as description changes, and major changes, like targets or the Bin changing, can all constitute version changes. With each version of a GTU, all of the product attributes can be stored along with that specific version.

As an example, if a product had its description changed by its laboratory, the change would be captured in its GTU, and the previous description would still be available. Thus, a more complete picture of the specific product becomes available to interested parties. GTUs can contain extensive information about their products, reflected in various fields. For example, GTUs can contain information about the product's Current Procedural Terminology (CPT) Code™, International Classification of Disease, Nth Revision, Clinical Modification (ICD9 or ICD9CM, or ICD10) Code, Unique Device Identification (UDI) Code, McKesson Z-Code™ Identifier, test code, Bin information, tax information, NPI code, version or timestamp, description, target gene, list price, other pricing data, time-to-results, laboratory code, the laboratory's internal test code, and other related data and information.

In some embodiments, a change to the test code for a product will trigger a disassociation of a product with its GTU. In other words, if everything about a product were to change, but the test code remained the same, the GTU value would stay the same and the version would be incremented to the current timestamp. In some embodiments, anomaly detection can be performed, whereby a reconciliation event may occur if certain conditions are met (e.g. % of targets changing). In some embodiments, GTUs can be managed via the "Diff" using a test collector module. Expert curators (human users) can be alerted to changes in a test via the Diff user interface.

By way of example and not limitation, the scraper 104, extractor 108, test collector 110, Diff 112, and disorder matching 114, and any other functional components for performing their respective functions, can reside in executable program modules (e.g., program modules 714 in FIG. 7) or other software constructs, or in dedicated programmed hardware components. These and other functional components of the embodiments described herein may be stored in memory devices (e.g., memory 704 or mass storage 712) and executable by processors (e.g., processing unit 702) of one or more computers, such as the computer 700 shown in FIG. 7. The cache 106 and/or database squid 116 can be implemented through one or more storage devices, such as in local electronic data storage devices (e.g., data store 716) or external electronic data storage devices such as remote databases. Although Bins and Binning will be described in further detail below, as a brief upfront discussion, when using the test collector in accordance with some embodiments, every product coming through the Diff that is added or modified that has been un-binned (targets/techniques change) can be checked to ensure that the GTU and bin association are accurate. GTU data can be stored with the products in the "squid", as will be described in further detail below and shown in FIGS. 3A-3D. In some embodiments, all versions of a product can be stored in the squid with a dropdown in a graphical user interface to access the data at specific points in time. Deprecated products may be stored in the squid as well, and can be clearly marked as deprecated. "Deprecated products" refer to products that are no longer available for sale on the market, but which are stored historically in various matching processes because they are of historical use.

According to some embodiments, GTUs are assigned automatically to new products. As mentioned in some detail above, in some embodiments, the assignment is based primarily on the product's test code. GTU assignment can be reviewed manually. Automatic assignment, automatic review, or manual review can result in reassignment of the product to an existing GTU, or assignment to a new GTU. In some embodiments, the GTU review process is managed using a Diff process, as will be described further below and with reference to FIGS. 2A and 2B. In some embodiments, manual review of GTUs is completed in the Diff user interface.

In some embodiments, a GTU is reviewed automatically by an algorithm when a product is changed by its offering laboratory. It may be automatically determined, for example, whether a different classification is needed for the GTU, or if the product needs a new GTU. This process can be verified by a user. This user verification can provide feedback to the system, which can incorporate the feedback into future determinations, enacting a machine learning process. In some embodiments, this process can take place in the Diff, test collector module, or both. In some embodiments, each GTU can be associated with its own JSON object.

In some embodiments, pricing data can be associated with a GTU through a process that may be referred to herein as price matching, which can associate pricing data using an algorithm. In some embodiments, price matching is accomplished using comma separate value (CSV) data, containing structured pricing information. This CSV data can come from, for example, price sheets provided by clients, including laboratories, hospitals, and other testing providers. In certain embodiments, this process can enable a user to find the best price for a desired result, for example, by allowing the user to sort testing products by price and provider. Price matching can be reviewed automatically. In some embodiments, machine learning can be incorporated to improve the results.

In some embodiments, information relating to the clinical disorders can be associated with a GTU through a process that may be referred to herein as disorder matching (see e.g., "Disorder matching" 114 in FIG. 1), which can associate a standardized disorder nomenclature with a GTU. In some embodiments, several different databases may be reconciled into a single graph database (e.g., ArangoDB) that allows standardized terminology to be applied consistently across laboratories. In some embodiments, disorder matching is accomplished using associations between disorder nomenclature used by laboratories, gene information, protein function information, including other data fields and standardized disorder terminology in a graph database. In certain embodiments, this process can enable a user to identify appropriate standardized disorder nomenclature for particular GTUs by traversing the graph using an algorithm.

Disorder matching can be reviewed automatically. In some embodiments, machine learning can be incorporated to improve the results.

In some embodiments, this information can be associated at a step after the "Diff" and GTU assignment. In some embodiments, this enables the assignment of current clinical nomenclature used to describe a disease state, which is subject to change, to a particular GTU during the time in which that GTU exists. Thus, once this current nomenclature enters the Squid, it becomes preserved during the time of that GTU's use, thereby creating a record.

Referring again to FIG. 1, a test collector 110 can perform functions that include automatically assigning products to Bins. Classification of products within a market can be complicated and based on a number of extrinsic factors that are relevant to a purchaser's use. Classification of genetic testing products can be especially challenging, given the variety of products and specific applications available within the market. Through the implementation of various embodiments described herein, providing accurate classifications can allow market participants to operate within a specific framework and understand more broadly where their products compete. In accordance with some embodiments of the present disclosure, a "binning" structure can be used for classifications.

A Bin as referred to herein can be considered a clinically comparable set of testing products that answer a set of clinically comparable questions. In accordance with some embodiments, testing products can be organized or sorted based on various factors or characteristics, such as test attributes. For example, laboratory testing products might be "binned" based on the specific gene(s) or analyte(s) they are targeted to detect. In some embodiments, a "target" factor relates to specific genes or analytes that are detected by the methodology of the testing product. Other factors that may be used include the methodologies used to obtain testing results, the specific disease or condition products are designed to address, and/or the specific clinical scenarios that the products are designed to address. For example, in some embodiments, a "techniques" factor relates to specific methodology that is used within the tests to determine a result, and a "disorders" factor relates to specific diseases/ conditions/clinical scenarios the products are designed to address.

According to some embodiments, Bins can have their scope determined in a way that allows testing products to be grouped effectively. Bin scope can be based on the same or different factors or characteristics used to place the laboratory testing products into Bins. For example, the scope of a Bin may be adjusted to conform to a change in the target gene(s) or analyte(s) a common or popular testing product is targeted towards. This could happen, for example, if it was discovered that multiple genes were commonly associated with the same medical condition, or, for example, if it became known that an additional gene or analyte was typically seen associated with a medical condition where that gene had not previously been associated. Other examples of reasoning for Bin changes include a change in preferred methodology or technique associated with a specific test generally and new or evolving preferences and trends amongst both consumers and medical care providers. Thus, Bins can be flexible and adaptable to changes in the market, for example the market for laboratory testing products. Bins can be combined or expanded and changed to suit the products on the market, for instance, such as changes due to methodology or product changes within the market. In some embodiments, retroactive traceability is maintained. A historical version of every bin can be made through time and the products contained within each bin can be maintained, thus providing a complete history of bins and products.

In some embodiments, products are classified into a single Bin, however Bins can contain many different, but similar products. This allows comparisons across products within single bins. Bins can also contain unique identifiers that are assigned on creation. Products can be initially classified into Bins when they are identified new in the market. In some embodiments, a Bin is automatically created by an algorithm when a new testing product requiring a new Bin is found. A new Bin can be created using an algorithm and then verified by an expert. As products change, their Bin status can be reviewed and a decision about a new classification may be made. The update can then be made to the Bin assignment.

If a new testing product is found that does not require a new Bin, no new Bin will be created, but instead the testing product will be automatically placed into its proper Bin via an algorithm. This process can be verified by a user. This user verification can provide feedback to the system, which can incorporate the feedback into future determinations, enacting a machine learning process. Machine learning used in matching products to bins, and refining product-to-bin matches, in some embodiments, can utilize search and graph theory, for example through the use of ElasticSearch. Other machine learning techniques that may be used include unsupervised clustering algorithms such as through the use of k-means, affinity propagation, and/or DBSCAN. In some embodiments, a Bin is reviewed automatically by an algorithm when a product within the Bin is changed by its offering laboratory. A system can automatically determine, for example, whether a new scope or classification is needed for the Bin, or if a new Bin needs to be created. This process can be verified by a user. This user verification can provide feedback to the system, which can incorporate the feedback into future determinations, enacting a machine learning process. In some embodiments, these processes can take place in the test collector 110.

Data integrity of the overall system can be maintained through both automated and focused expert processes. The overall database of laboratory testing products, Bins, GTUs, and associated information can be routinely reviewed for errors and changes. In some embodiments, algorithms are used to routinely crawl through the overall dataset looking for mis-classifications, mis-binning, necessary changes in the scope of Bins, and errors within the products themselves. In some embodiments, algorithms that may incorporate machine learning can be used to automatically make changes to correct the issues or "flag" the issue for review and correction by a user such as an expert reviewer. Periodic review of Bins can occur on a regular basis, for example monthly. Clinical, technical, and market experts can review Bins identified by manual flagging or algorithms to sit outside the context of defined marketplace parameters. These can then be resolved and changes made. Referring to the screen shot of FIG. 3C, in some embodiments, this process takes place in the database "squid", which can utilize an interface that allows users to drag and drop individual products between Bins. The squid interface can be configured to allow an analyst (i.e., human user) to change the Bins in an on-the-fly manner to reorganize as desired and appropriate. For instance, in circumstances where two Bins which are very similar were identified through a process, all of the products in the two Bins can be moved into a single Bin, and then a GTU can be reassigned accordingly. In some embodiments, each Bin can be associated with its own JSON object.

In some embodiments, additional classification structures may be built on top of other data associated with GTUs, Bins, and other data that is stored or generated within the system. This data may be associated with its own JSON object and may utilize some of the components as outlined in this system. Certain classifications can themselves be further classifiable based on certain criteria such that a hierarchical classification structure/arrangement exists. There can thereby be a hierarchy of layers, which may include a domain layer in which a domain can be considered a larger grouping of categories. These classification systems may contain information about the product's intended use, clinical classification, clinical scope, and other additional types of classification, for instance. The classifications can be according to, for example: clinical scope corresponding to clinical practice for particular specialties or sub-specialties of medical usage, and/or market scope as it relates to, for instance, competition amongst a group of laboratories in a particular market, health plans, or other related entities that would utilize the relevant information according to such embodiments in the normal course of business.

Figure 2A:
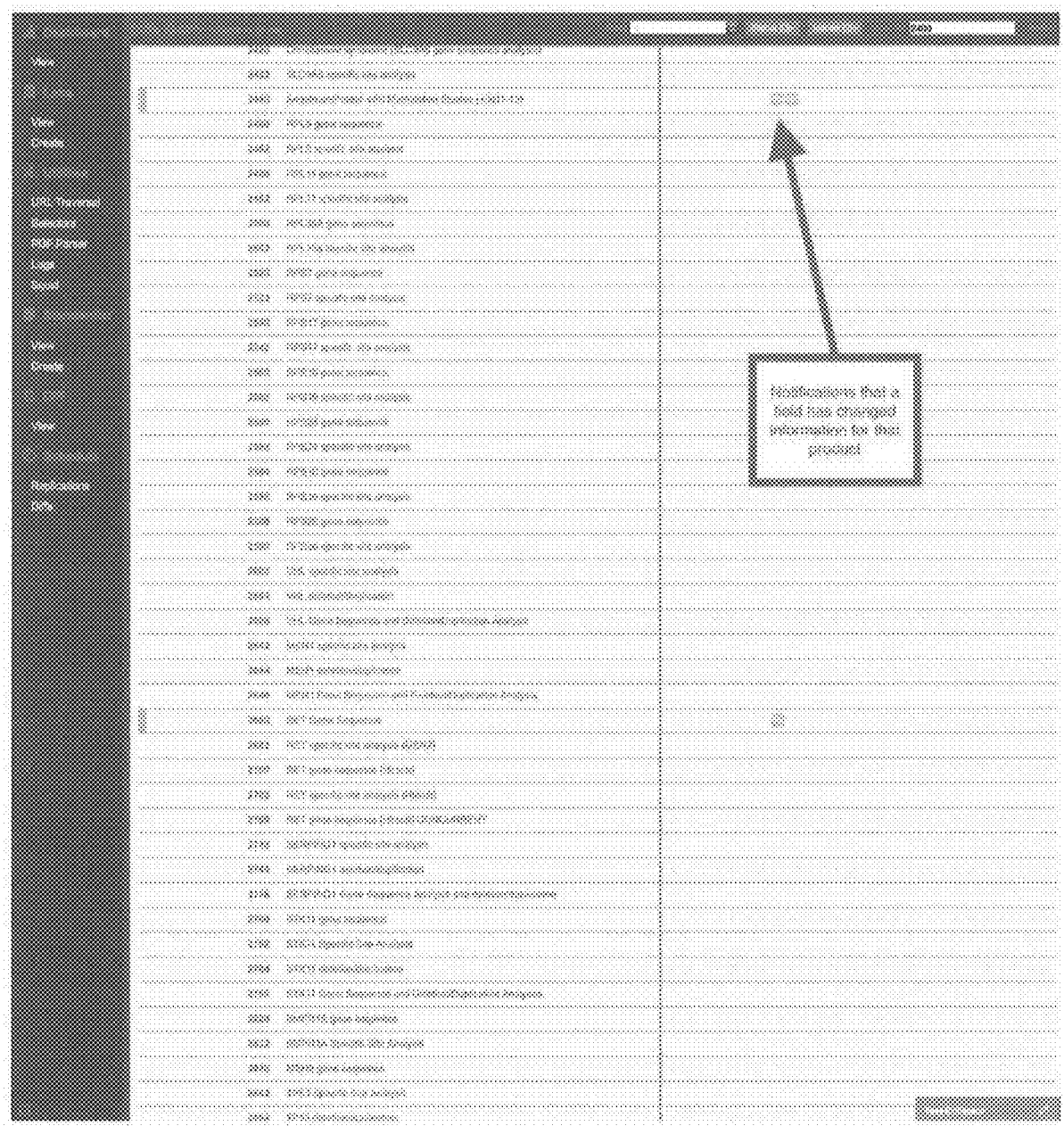
Figure 2B:
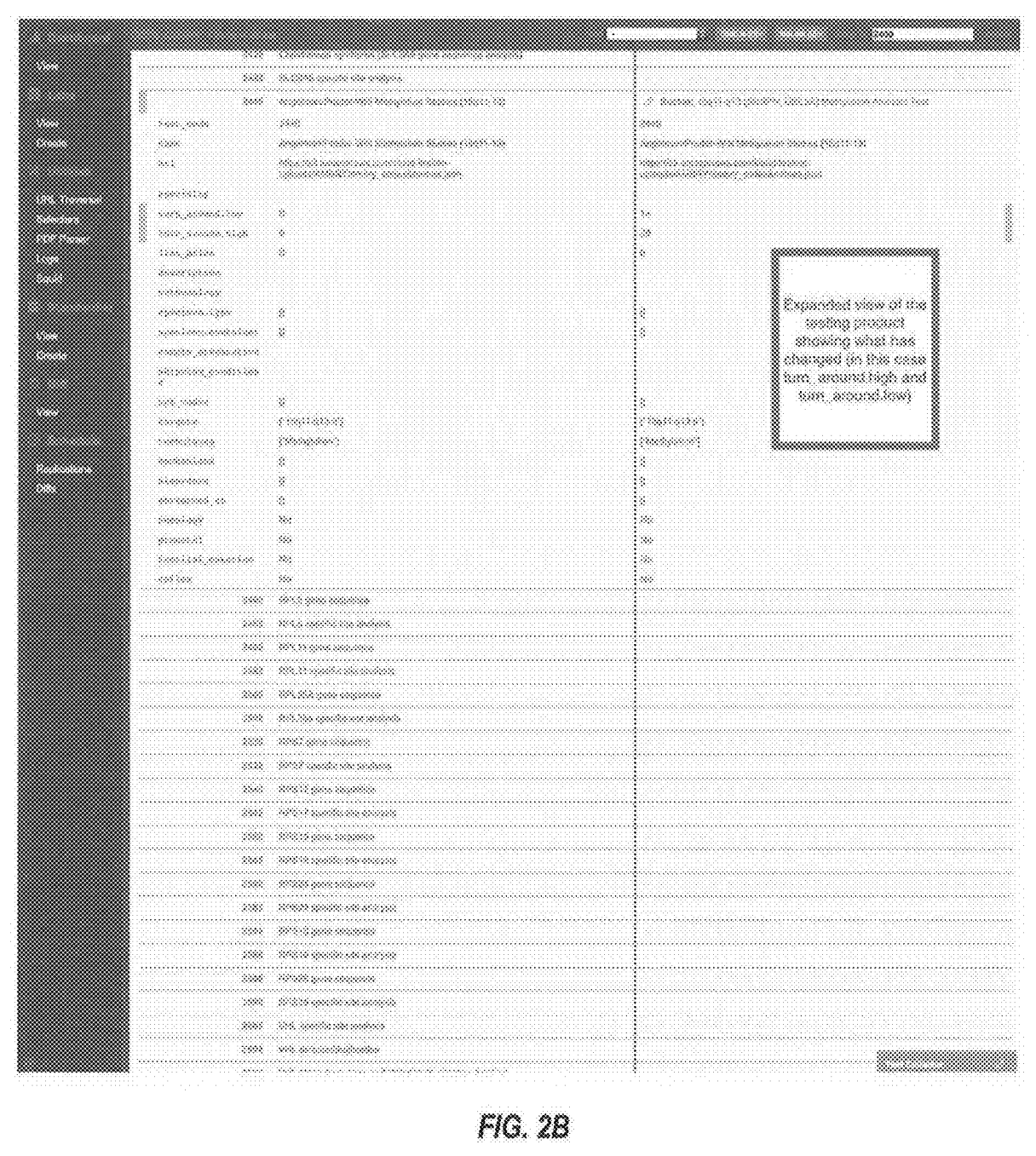

FIGS. 2A and 2B are screen shots illustrating various aspects relating to "Diff" associated with testing products, in accordance with example embodiments of the present disclosure. In particular, FIGS. 2A and 2B illustrate screen shots of a dashboard of a graphical user interface tool showing various listed testing products by test code and name, as well as corresponding fields of data for each testing product. "Diff"-related functionalities described herein with respect to certain embodiments can involve the identification of changes in product information over time, as reflected in changes in the information shown in the data fields. This can also include the removal or addition of information in each of these fields. It also can include information about validation errors or errors in matching to a standardized term.

FIG. 2A illustrates a listing of testing products, organized in rows with a test code and name in a left column and a corresponding set of indicators for the various fields for each product, listed horizontally across the row. For example, one listed test product is listed by test code "2440" and the name "Angelman/Prader-Willi Methylation Studies 15q11-13". In the corresponding right column, as noted by the comment box and attached arrow inserted into the diagram, information has changed for two particular fields. As shown, the fields are visually emphasized by highlighting them (see "TAL" and "TAH"). Another listed test product has test code "2680" and the name "RET Gene Sequence". In the right column, as shown there is a highlighted indicator "TAL". FIG. 2B shows the listed test product for test code 2440 mentioned above, but in an expanded view which shows the fields and corresponding details. As illustrated in the expanded view (and as noted in the comment box inserted into the diagram), there is an indication that information for the field "turn_aroundlow" (abbreviated by "TAL" in the view of FIG. 2A) has changed to a value of 14 (in the view of FIG. 2B), and also an indication that information for the field "turn_around.high" (abbreviated by "TAH" in the view of FIG. 2A) has changed to a value of 28 (in the view of FIG. 2B).

It should be noted that the comment box and attached arrow in FIG. 2A ("Notifications that a field has changed information for that product") is intended for purposes of labeling elements of the illustrated embodiment of the present disclosure for convenience of the reader, and does not in itself constitute any substantive element of the embodiment shown. Similarly, the comment box in FIG. 2A ("Expanded view of the testing product showing what has changed (in this case turn_around.high and turn_around.low") is intended for noting aspects of the illustrated embodiment of the present disclosure for purposes of convenience of the reader, and does not in itself constitute any substantive element of the embodiment shown.

According to some embodiments, the entire database of information (e.g., information regarding the laboratory testing products, their processed information, and the historical data associated with that information) can be maintained in a database squid 116 (FIG. 1). As shown in the screen shots of FIGS. 3A-3D and further described below, the squid 116 can provide contextual information for users making manual updates to the information in the system, including updates to GTUs and Bins.

In some embodiments, the squid 116 is a database that can store and maintain both a current record and backup record of all the information regarding testing products. The backup can be a historical record which can be used in making determinations, for example, during the matching processes or Diff process. In some embodiments, the squid 116 will allow access to the backup via a graphical user interface that comprises a dropdown menu. Such a menu can allow for a user to access the backup and to select between various saved versions of the historical data of a specific test product, or the information regarding testing products as a whole. Access to this information can allow the user to fully understand the product and how it has evolved, facilitating a more accurate review of the product and facilitating a more accurate edit of the product, if necessary.

In some embodiments, the squid 116 interface allows a user to understand and identify detailed information about individual products and services. In some embodiments, a user can examine these products as curated within individual Bins or other groupings. Although some embodiments described herein and as shown in FIG. 1 show the squid and Diff as separate components, in other embodiments, the interface may comprise a "collections" view, whereby different standardization functions can be performed within the same interface, i.e. various functions that in some embodiments are performed in a Diff interface and a separate squid interface can be performed using an integrated, consolidated interface view.

Figure 3A:
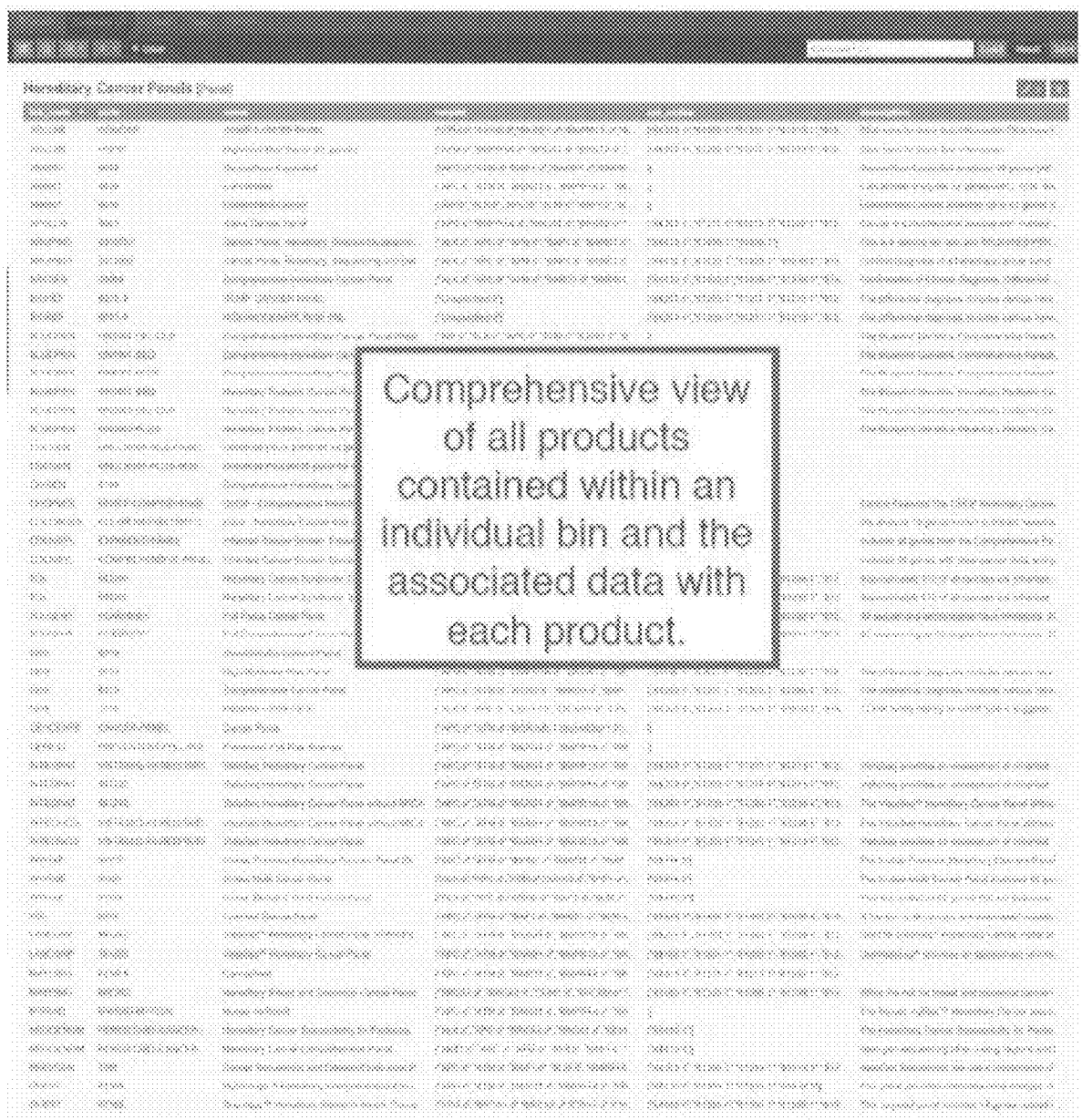
FIGS. 3A-3D are screen shots illustrating various aspects relating to a database "squid" interface in accordance with some embodiments of the present disclosure.
Figure 3B:
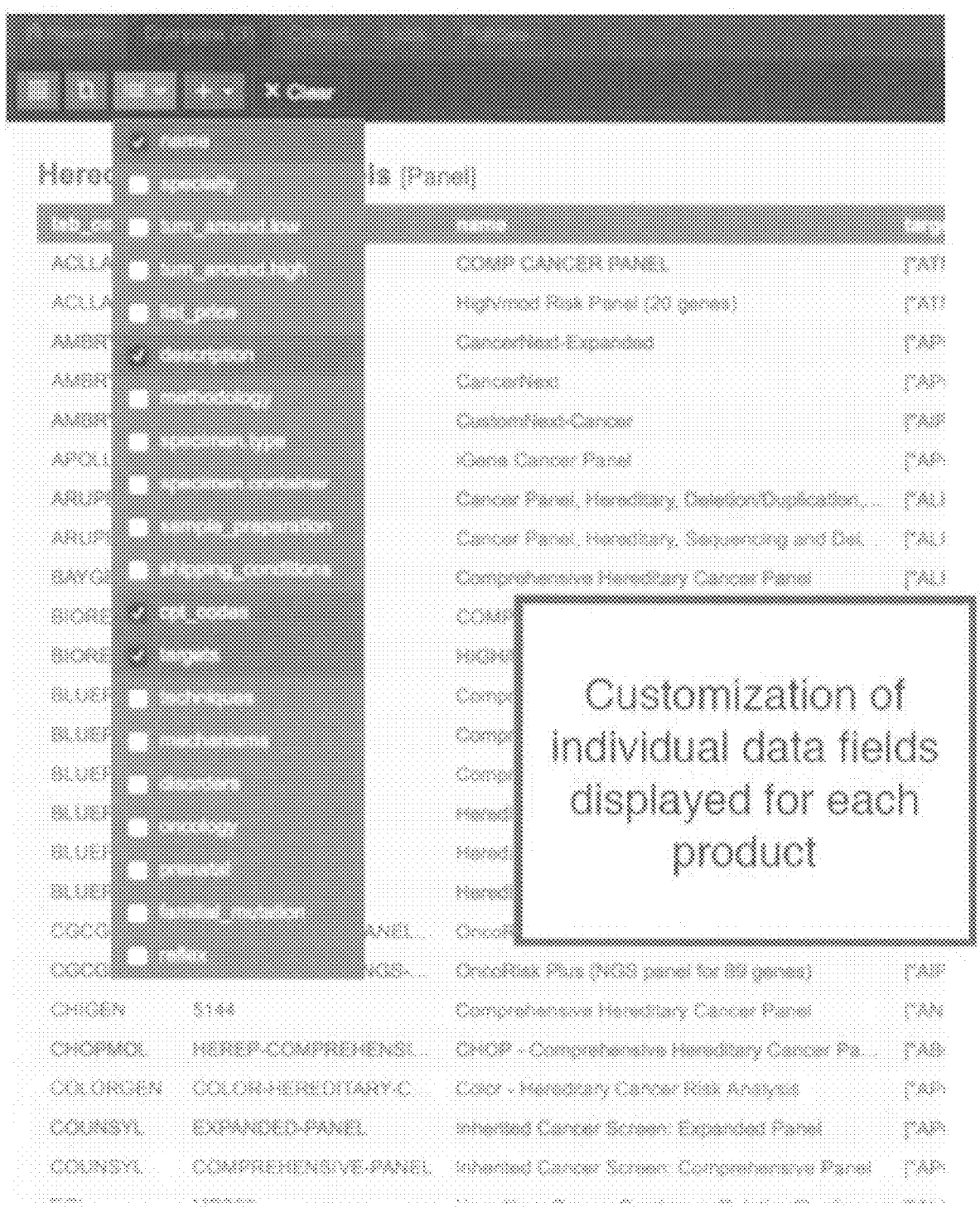
Figure 3C:
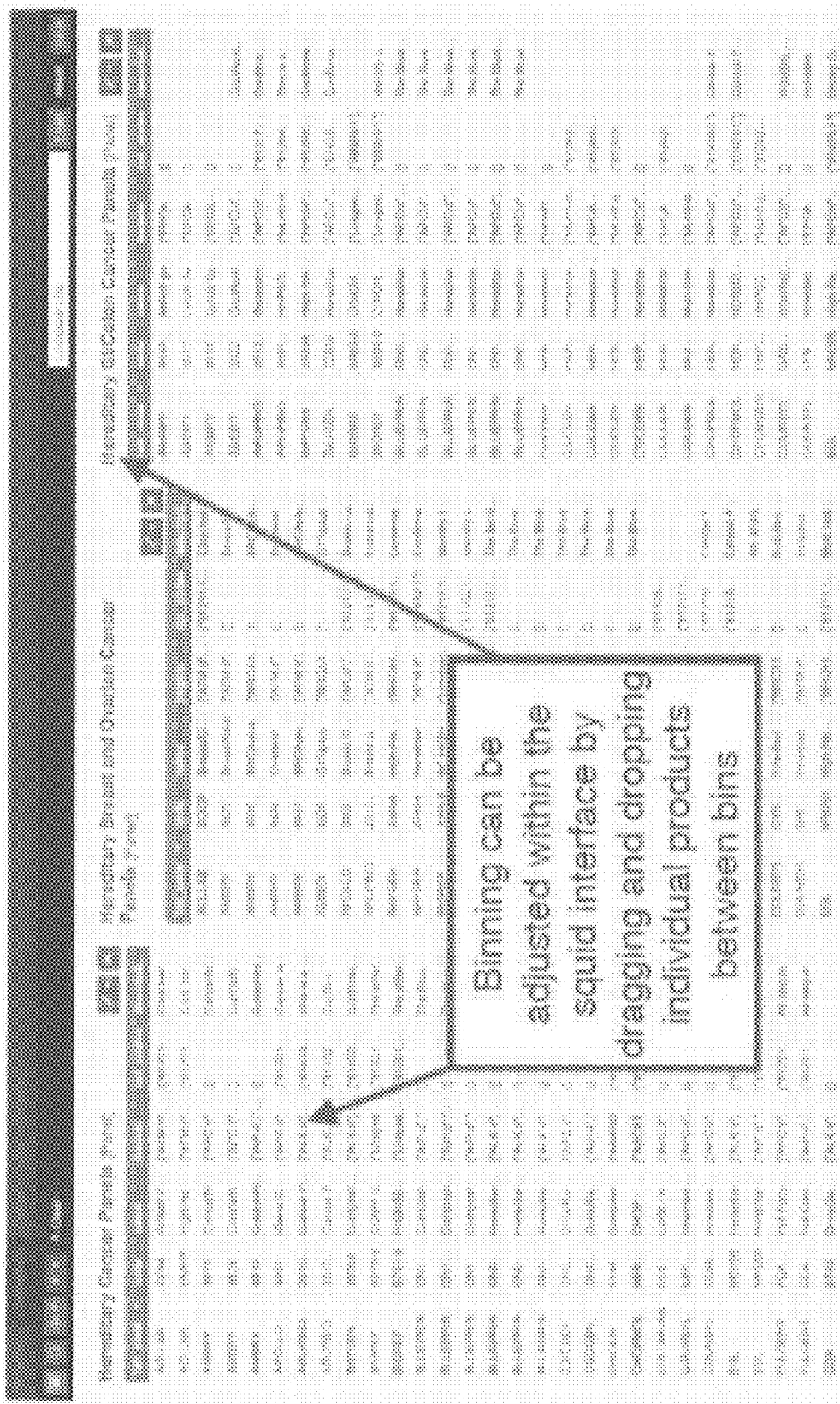
Figure 3D:
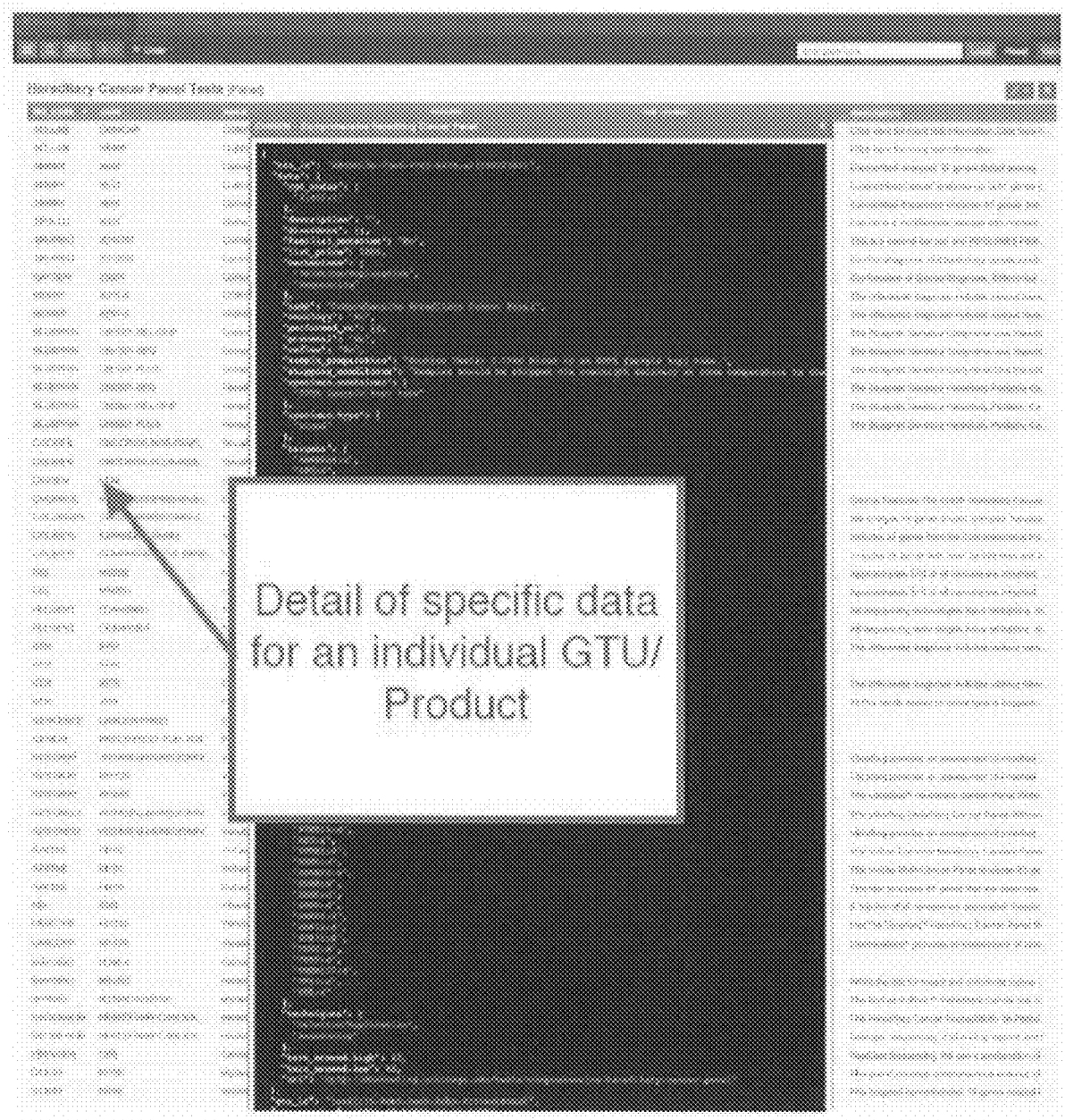

FIG. 3A shows a screen shot detailing characteristics and data fields about individual testing products as shown in the squid interface. As illustrated, individual testing products and their data fields are detailed as individual rows in the table. FIG. 3B shows a screen shot detailing a customization of the fields displayed for each product. In some embodiments, this allows an individual user to customize the data fields within their view for the particular application. FIG. 3C shows a screen shot detailing binning adjustments between products. In some embodiments, users may move individual products between Bins in order to adjust the composition of Bins for a variety of reasons. FIG. 3D shows a screen shot detailing a specific data object relevant to an individual GTU or product. This allows a user to access the raw data object if necessary for their particular application. It should be noted that the comment boxes and/or arrows in FIGS. 3A-3D are intended for purposes of labeling elements and/or noting aspects of the illustrated embodiment of the present disclosure for purposes of convenience of the reader, and do not in themselves constitute any substantive elements of the embodiments shown (see FIG. 3A, "Comprehensive view of all products contained within an individual bin and the associated data with each product"; FIG. 3B, "Customization of individual data fields for each product"; FIG. 3C, "Binning can be adjusted within the squid interface by dragging and dropping individual products between bins", and attached two arrows; and FIG. 3D, "Detail of specific data for an individual GTU/Product", and attached arrow).

FIG. 4 illustrates a claims matching process 400 for matching a claim to a product and/or Bin, in accordance with some embodiments of the present disclosure. Matching of a claim object with a product and/or Bin can allow the user to understand the relationship between the original claim (that was used to create a claim object) and the payment for the desired testing product; it can be considered a reconciliation between a billing system nomenclature and the products or services on the market. This is helpful because of the increasingly unmanageable number of unique genetic testing and other testing products aimed at personalized medicine. That is, as genetic testing has become increasingly common and popular, the number of tests has grown to over 65,000, with an average of ten new tests entering the market daily. All of these tests represent over 14,000 distinct, clinically relevant categories. This rapid growth has made it increasingly difficult to accurately manage ordering, billing, and reimbursement of the tests.

An incoming claim is used to create a claim object. The claim object can be created by associating a testing product's information into the claim object. In some embodiments, the associated testing product information is structured to allow for an algorithm to match the structured data to a testing product or GTU. As shown in FIG. 4, a raw claim file 402, such as an electronic medical claim in electronic form, can be put through a de-identification step 404 to remove all personal identifiers from the claim file, thereby creating a de-identified claim file 406. The de-identified claim file 406 can then be used to create the claim object at 408.

Now referring to building a claim object (see 408), in some embodiments, the claim object can include a unique claim identifier for each claim and provider identifiers, which essentially can serve to indicate what product or service was ordered and represented by a particular claim. The provider identifiers can include Tax ID, NPI, and provider name, together creating a provider identification. The claim object can be created by incorporating this information, along with CPT Codes, ICD9/ICD10 Code, service unit(s), modifier codes, and other related information associated with the individual claim in a structured format. A CPT signature can be created from the billing code (HCPCS, CPT code, Z-code) and service units, to create a data object representing, for instance, how many of each billing code was billed for a particular service. In some embodiments, the structuring of this information can occur through an algorithm that is designed to create a unified and consistent representation of an individual claim from across multiple disparate health plan claim accounting systems. In some embodiments, the algorithm can be enhanced using machine learning processes, such as those as will be described in further detail below.

In some embodiments, an algorithm may access an electronic database containing associations of information related to a testing company or a laboratory (e.g., National Provider Identification (NPI) number, tax information, or other company/laboratory specific information). The algorithm can then associate a specific testing product with a specific testing company and/or laboratory using the information available to it (see 410). In some embodiments, this is a standardized identifier for a particular laboratory entity that is maintained through the system described in 108. In some embodiments, this process can be checked manually. In some embodiments, the algorithm can be enhanced using one or more machine learning processes. A claim object can then be used to facilitate product matching 412a or Bin matching 412b (collectively 412). The product matching process 412a can automatically search an index and associate the claim object with the product, which can already be associated with a Bin. The product can be previously associated with a Bin in the test collector module (see, e.g. 110 in FIG. 1), as outlined above. In matching to a product, the exact GTU that was ordered can be identified, using a combination of machine learning and search, and a particular Bin can then be derived. In the product matching process 412a, in some embodiments, product information from the squid (see 414) or a data representation in the squid can also be utilized. In some embodiments, if the structured testing product information cannot be matched to a specific product by the algorithm, then the claim object is matched to a Bin (see 412b). This may happen, for example, if the testing company or the laboratory completing the test is not clear, i.e., information is too vague or there is an anomaly. In some embodiments, one or more machine learning enhanced algorithms can be used to enhance the product matching, Bin matching, or both. In some embodiments, this process can be reviewed manually.

By way of example and not limitation, the components illustrated by blocks corresponding to de-identification 404, build claim object 408, matching laboratory provider to standard identifier 410, product matching 412a and/or bin matching 412b, and expert review 416, and any other functional components for performing their respective functions, can reside in executable program modules (e.g., program modules 714 in FIG. 7) or other software constructs, or in dedicated programmed hardware components. These and other functional components of the embodiments described herein may be stored in memory devices (e.g., memory 704 or mass storage 712) and executable by processors (e.g., processing unit 702) of one or more computers, such as the computer 700 shown in FIG. 7. The database squid 116 and analytics database 418 can be implemented through one or more storage devices, such as in local electronic data storage devices (e.g., data store 716) or external electronic data storage devices such as remote databases.

Various machine learning processes/algorithms may be utilized for implementing some aspects of the present disclosure. For example, in some embodiments, product matching 412a and/or Bin matching 412b can be performed by using a random forest algorithm, wherein a claim comes in, is matched to a product and/or Bin based on a training data set that has been developed which creates a kind of random forest model, and the claim is then run through the model. In some embodiments, a table of matches that may use signatures to products and/or bins can be built up over time, which can be built in SQL (structured query language). The built-up, known matches table can be used as a training data set for running machine learning algorithm(s) to perform matching of remaining, unmatched claims, for example by using a random forest model. As will be recognized by those skilled in the art, random forest techniques (also referred to as random decision forests) relate to ensemble learning method which constructs a plurality of decision trees at training time and outputs the class that is the mode of the classes/classification or mean prediction/regression of individual trees.

In accordance with some embodiments, claims information can be run through a random forest approach, and then identified accurate or otherwise desirable matches that are achieved can then be used for further training data sets in subsequent iterations of the respective machine learning model. Alternative approaches utilizing machine learning that may be utilized include techniques that may use search algorithms of ElasticSearch.

For product matching 412a, a search interface can be used. It should be appreciated that many different types of machine learning algorithms can be utilized. As described in some detail above, in product matching, a claim object is analyzed to look at the CPT signature, look at the service units and the ICD 9/10 codes, and determine what product is most likely represented by a signature. It also can incorporate laboratory information indicating who has performed a service. Expert review steps (see expert review 416) can be used to either validate or make corrections, and all the metadata can go back into training those algorithms.

Figure 5A:
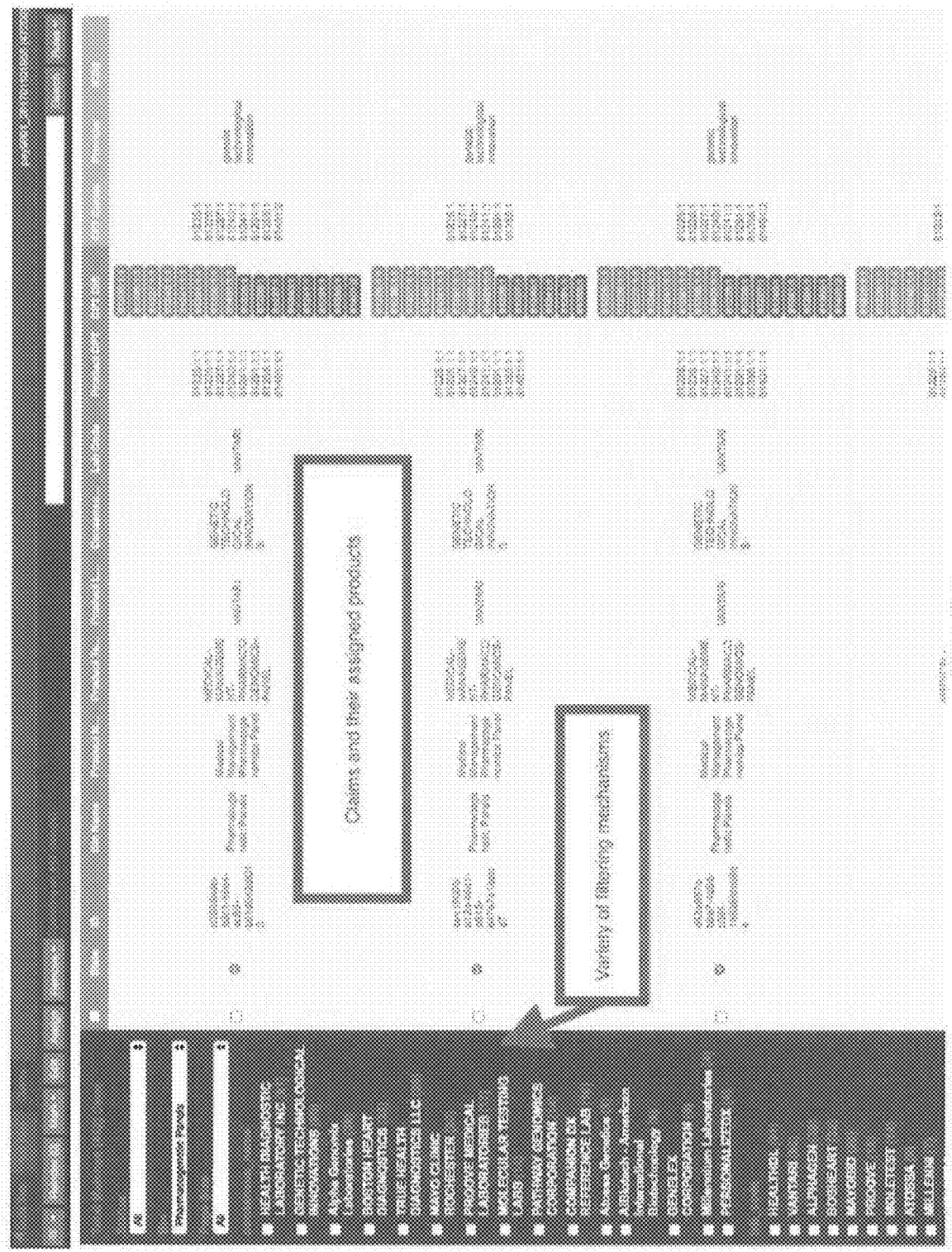
FIGS. 5A and 5B are screen shots illustrating various aspects of expert review in accordance with some embodiments of the present disclosure.
Figure 5B:
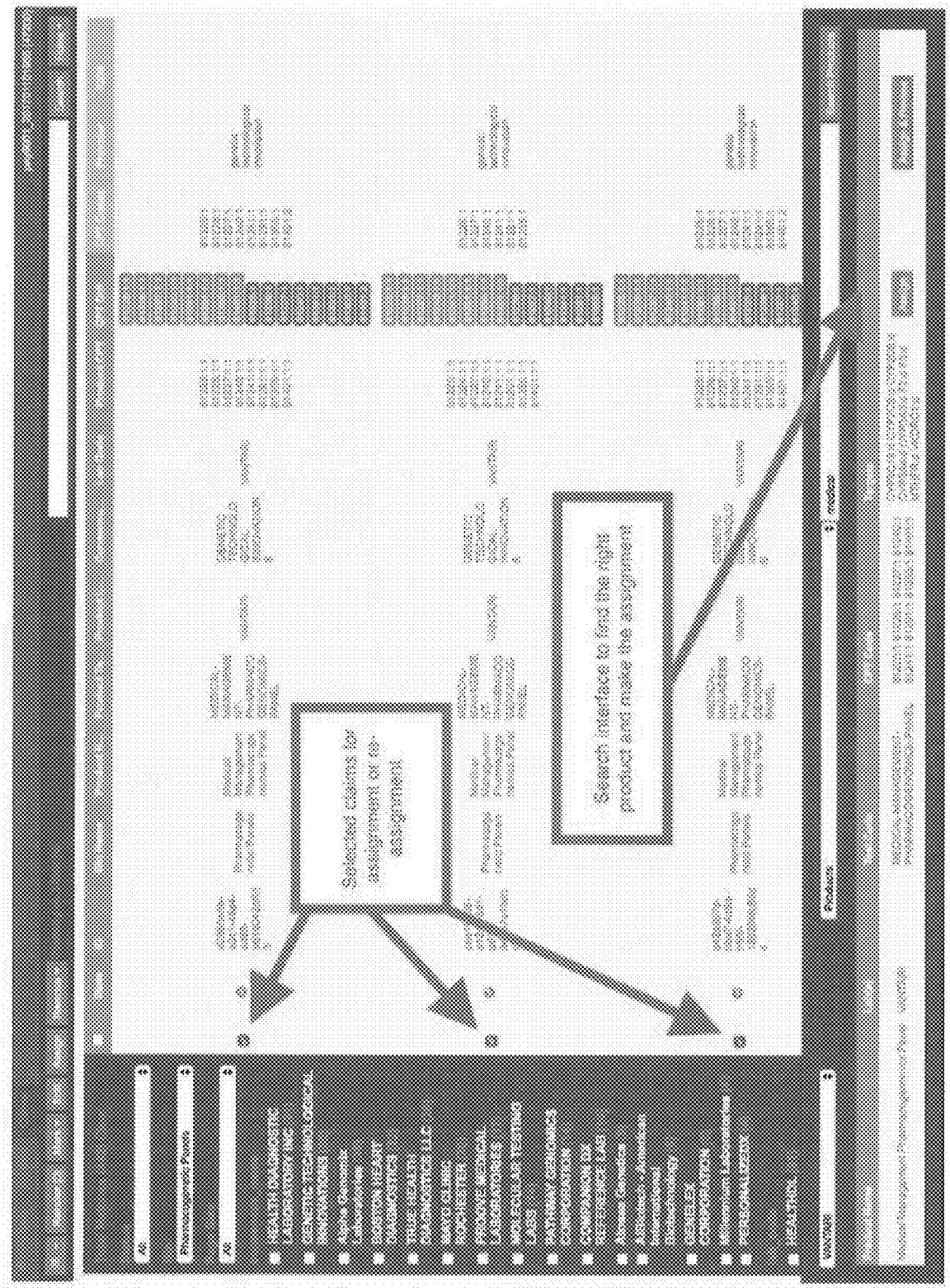

In some embodiments, the results of the product matching 412a or Bin matching 412b processes can then be reviewed by a user in a process that, for some embodiments, is referred to herein as "expert review" 416, as shown in FIGS. 5A and 5B and described in further detail below. Data resulting from expert review can be saved and used to refine algorithms in a feedback loop, i.e., the algorithm can be given feedback to optimize its association of the claim object, thus enacting a machine learning process.

In some embodiments, in expert review 416, the individual product and/or bin matches can be reviewed by an expert user to refine and revise matches. In some embodiments, an individual user can utilize an interface designed to alter and correct these matches, as shown in FIGS. 5A and 5B. The matched claim information can then be stored in a broader analytics database 418, and joined back with other information contained within the identified claim file to provide a more comprehensive version of the actual claim.

FIGS. 5A and 5B are screen shots illustrating an interface for, and various aspects of, expert review in accordance with example embodiments of the present disclosure. In some embodiments, individual product matches can be reviewed by an expert user to refine and revise product matches. In some embodiments, an individual user can utilize an interface designed to alter and correct these matches. FIG. 5A shows de-identified claim objects that, in some embodiments, have been previously associated with an individual testing product. In some embodiments, a variety of filtering mechanisms enable the user to filter and identify the specific claims they are currently manipulating in the interface. FIG. 5B shows a selected set of claim objects, with their associated product information that have been identified for re-assignment. In some embodiments, a search interface allows the user to access and filter product information from the squid (see, e.g., 116 in FIG. 1) to assign a GTU to the individual claim. It should be noted that the comment boxes and/or arrows in FIGS. 5A and 5B are intended for labeling elements and/or noting aspects of the illustrated embodiment of the present disclosure for purposes of convenience of the reader, and do not in themselves constitute any substantive elements of the embodiments shown (see FIG. 5A, "Claims and their assigned products" and "Variety of filtering mechanisms" and attached arrow; and FIG. 5B "Selected claims for assignment or re-assignment" and attached arrows, and "Search interface to find the right product and make the assignment" and attached arrow).

In some embodiments, an algorithm may identify and create claim objects from across multiple individual claims. In some embodiments, this process can then be reviewed by a user. In some embodiments, the algorithm can be given feedback to optimize its association of the claim object. In some embodiments, an algorithm may associate a single claim with a combination of multiple GTUs to create multiple claim objects. In some embodiments, this process can then be reviewed by a user. In some embodiments, the algorithm can be given feedback to optimize its association of the claim object.

According to some embodiments, reports can be generated based on inquiries. For example, a report could be generated that provides information about all of the testing products that will accomplish the desired purpose of the test. This could be, for example, testing of a specific gene. These tests could be sorted, for example, by price, thus enabling the report recipient to make a more educated decision in purchasing or using testing products. For example, the reports could be tailored to examine specific testing companies or laboratories in an effort to combat fraud or eliminate wasteful spending. In some embodiments, various reports can be generated from data in the analytics database, and there can be a user interface provided for a client to access and interact with the analytics database.

According to some embodiments, an interface can be developed and applied to generate reports based on inquiries. In some embodiments, these reports can be delivered in a flexible manner that allows a user to write and define their own inquiries into the specific datasets. For example, multiple end users can access a variety of reports within custom dashboards.

Figure 6:
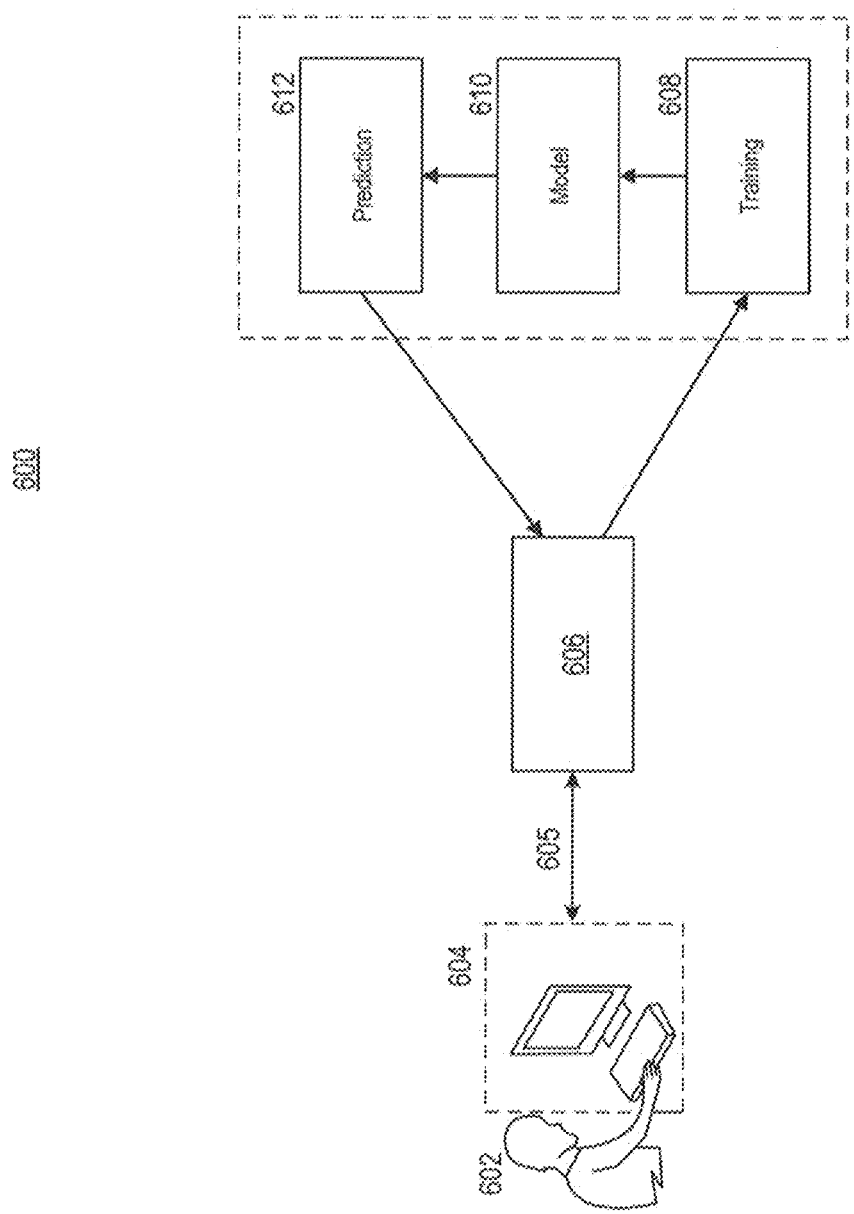
FIG. 6 is a diagram of a system for machine learning capable of implementing one or more embodiments.

FIG. 6 is a diagram illustrating architecture of an exemplary system 600 for machine learning in which one or more example embodiments described herein may be implemented. For example, one or more components and aspects of the system 600 may be used in the product and/or Bin matching processes and/or expert review as described above in various embodiments. Under supervised learning, human users may provide examples of changes and their corresponding desired result. For example, when a specific genetic test is changed by a laboratory or test provider (e.g., a change in the scope of target genes), machine learning can be used to improve the efficacy of re-matching that test with its associated product and Bin.

As shown, the system 600 includes a user computer 604 operated by a user 602. The user computer 604 can include some or all of the components of the computer 700 shown in FIG. 7 and described in further detail below. A user interface such as a graphical user interface executing on the computer 604 may be configured to receive user input 605. By interacting with the user interface of the user computer 604, the user 602 may perform, via a model training client 606, functions associated with model training in machine learning, according to some embodiments described herein. The user interface may provide one or more functionalities associated with the user interfaces shown in FIGS. 2A, 2B, 3A-3D, 5A, 5B, and 10-14.

A base model (see model 610) may be used to make first "predictions" on a first set of data, for example a decision that a particular data item corresponds to and should be matched to a particular product or service, or that a particular claim should be matched to a particular product or Bin. A user 602 such as an analyst may then correct incorrect results from the first predictions. The corrected data may then be used to train (see "training 608") to produce a new model (e.g., enhanced, improved, further trained model of model 610) based on the corrections made to the first data. This new model may then be used to make predictions on second data, and so on accordingly. This prediction, correction, and training process may progressively improve a model as additional items are processed. In some embodiments, one or more functions of the training, prediction, and feedback processes may be unsupervised, for example they may be performed autonomously by computer without user intervention.

As discussed above with respect to various implementations, various machine learning processes/algorithms may be utilized for implementing aspects of the present disclosure. For example, in some embodiments, product matching and/or Bin matching (see, e.g., FIG. 4) can be performed by using a random forest algorithm, wherein a claim comes in, is matched to a product and/or Bin based on a training data set that has been developed which creates a kind of random forest model, and the claim is then run through the model. In some embodiments, a table of matches that may use signatures to products and/or bins can be built up over time, which can be built in SQL (structured query language). The built-up, known matches table can be used as a training data set for running machine learning algorithm(s) to perform matching of remaining, unmatched claims, for example by using a random forest model. In accordance with some embodiments, claims information can be run through a random forest approach, and then identified accurate or otherwise desirable matches that are achieved can then be used for further training data sets in subsequent iterations of the respective machine learning model.

Alternative approaches utilizing machine learning that may be utilized include techniques that may use search algorithms of ElasticSearch. Machine learning used in matching products to bins, and refining product-to-bin matches, in some embodiments, can utilize search and graph theory, for example through the use of ElasticSearch. Other machine learning techniques that may be used include unsupervised clustering algorithms such as through the use of k-means, affinity propagation, and/or DBSCAN. In accordance with some embodiments, one or more aspects of neural networks can be utilized, for example to take and weight different diagnosis codes, procedure codes, and laboratory names and allow for the exploration around more of the parameter space around diagnosis codes.

Figure 7:
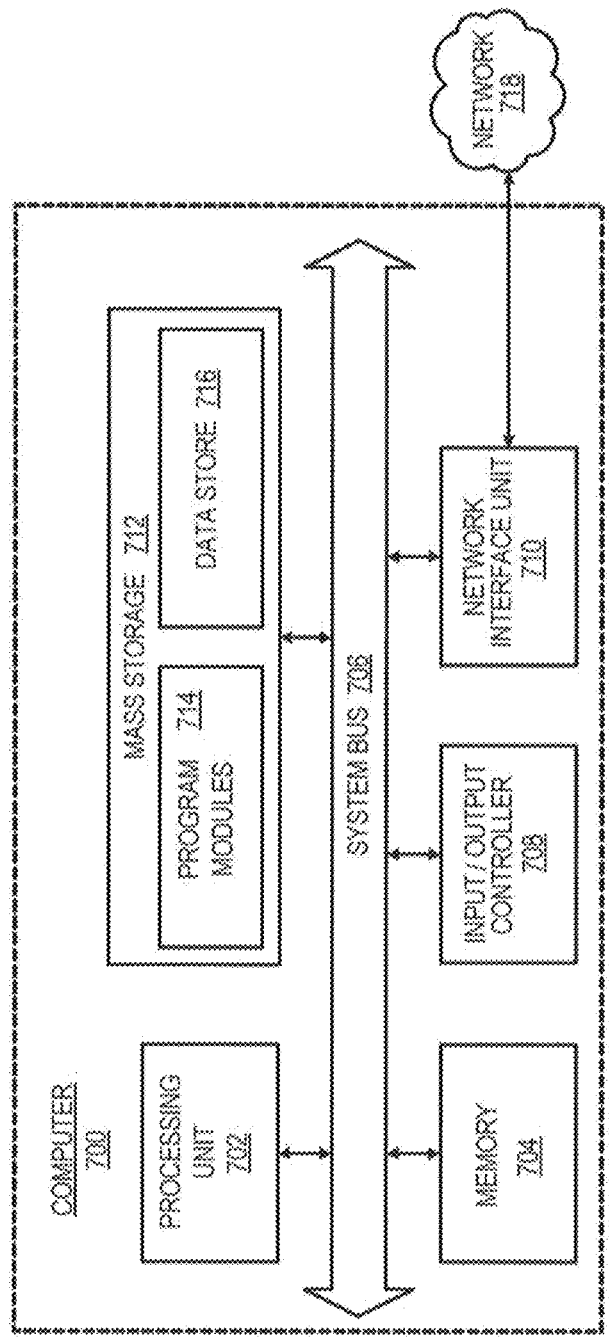
FIG. 7 is diagram illustrating a computer hardware architecture for a computing system capable of implementing one or more embodiments.

FIG. 7 is a computer architecture diagram showing a general computing system capable of implementing one or more embodiments of the present disclosure described herein. A computer 700 may be configured to perform one or more functions associated with embodiments illustrated in one or more of FIGS. 1-6 and 8-14. It should be appreciated that the computer 700 may be implemented within a single computing device or a computing system formed with multiple connected computing devices. For example, the computer 700 may be configured for a server computer, desktop computer, laptop computer, or mobile computing device such as a smartphone or tablet computer, or the computer 700 may be configured to perform various distributed computing tasks, which may distribute processing and/or storage resources among the multiple devices.

As shown, the computer 700 includes a processing unit 702, a system memory 704, and a system bus 706 that couples the memory 704 to the processing unit 702. The computer 700 further includes a mass storage device 712 for storing program modules. The program modules 714 may include modules executable to perform one or more functions associated with embodiments illustrated in one or more of FIGS. 1-6 and 8-14. The mass storage device 712 further includes a data store 716.

The mass storage device 712 is connected to the processing unit 702 through a mass storage controller (not shown) connected to the bus 706. The mass storage device 712 and its associated computer storage media provide non-volatile storage for the computer 700. By way of example, and not limitation, computer-readable storage media (also referred to herein as "computer-readable storage medium" or "computer-storage media" or "computer-storage medium") may include volatile and non-volatile, removable and non-removable media implemented in any method or technology for storage of information such as computer-storage instructions, data structures, program modules, or other data. For example, computer-readable storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 700. Computer-readable storage media as described herein does not include transitory signals.

According to various embodiments, the computer 700 may operate in a networked environment using connections to other local or remote computers through a network 718 via a network interface unit 710 connected to the bus 706. The network interface unit 710 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems.

The computer 700 may also include an input/output controller 708 for receiving and processing input from a number of input devices. Input devices may include, but are not limited to, keyboards, mice, stylus, touchscreens, microphones, audio capturing devices, or image/video capturing devices. An end user may utilize such input devices to interact with a user interface, for example a graphical user interface on one or more display devices (e.g., computer screens), for managing various functions performed by the computer 700, and the input/output controller 708 may be configured to manage output to one or more display devices for visually representing data.

The bus 706 may enable the processing unit 702 to read code and/or data to/from the mass storage device 712 or other computer-storage media. The computer-storage media may represent apparatus in the form of storage elements that are implemented using any suitable technology, including but not limited to semiconductors, magnetic materials, optics, or the like. The program modules 714 may include software instructions that, when loaded into the processing unit 702 and executed, cause the computer 700 to provide functions associated with embodiments illustrated in FIGS. 1-6 and 8-14. The program modules 714 may also provide various tools or techniques by which the computer 700 may participate within the overall systems or operating environments using the components, flows, and data structures discussed throughout this description. In general, the program module 714 may, when loaded into the processing unit 702 and executed, transform the processing unit 702 and the overall computer 700 from a general-purpose computing system into a special-purpose computing system.

The processing unit 702 may be constructed from any number of transistors or other discrete circuit elements, which may individually or collectively assume any number of states. More specifically, the processing unit 702 may operate as a finite-state machine, in response to executable instructions contained within the program modules 714. These computer-executable instructions may transform the processing unit 702 by specifying how the processing unit 702 transitions between states, thereby transforming the transistors or other discrete hardware elements constituting the processing unit 702. Encoding the program modules 714 may also transform the physical structure of the computer-readable storage media. The specific transformation of physical structure may depend on various factors, in different implementations of this description. Examples of such factors may include, but are not limited to: the technology used to implement the computer-readable storage media, whether the computer-readable storage media are characterized as primary or secondary storage, and the like. For example, if the computer-readable storage media are implemented as semiconductor-based memory, the program modules 714 may transform the physical state of the semiconductor memory, when the software is encoded therein. For example, the program modules 714 may transform the state of transistors, capacitors, or other discrete circuit elements constituting the semiconductor memory.

As another example, the computer-storage media may be implemented using magnetic or optical technology. In such implementations, the program modules 714 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present disclosure.

Some aspects of the present disclosure relate to health plans and policies, and to determining whether a policy covers particular medical products or services, for example genetic testing related products or services. A health plan policy (also referred to herein as "health policy" or "policy") can be considered to be a compilation of the medical requirements and billing requirements for a provider to receive reimbursement. In some embodiments, health plan policies are broken down into discrete elements that can be aligned with a particular taxonomy, with a process for creating, storing, and updating the discrete elements, and in some embodiments, the present disclosure relates to utilizing a combined representation (e.g., GTU, category, policy) in an automated process for reviewing claims for eligibility, payment, fraud, waste, and/or abuse, and for enabling the ordering of tests in a provider's workflow. Among other advantages and benefits provided by certain embodiments of the present disclosure, coverage outcome algorithms (COAs) can be generated and utilized to address the variability in the market with regard to how health plans can structure policies.

Certain categorizations applied to particular policies can be utilized for activating a determination and correlation with respect to existing identifiers, for example Bins (e.g., via Bin identifiers) and/or GTUs as discussed above with respect to other aspects and embodiments of the present disclosure, and with respect to coverage or a certain range of tests or services. With respect to categorization (binning) of a particular test into a type of tests, a policy can be associated with similar types of tests in the certain category. As some examples, some tests may be categorized in terms of the particular gene that they all test for. In some embodiments, aspects of one or more of these processes can utilize generated coverage outcome algorithms (COAs).

Based on what are sometimes referred to herein as "triggers", interactive tools may be provided for an end user who desires to evaluate whether a particular condition and/or associated medical products or services associated with the condition, are covered by a particular health plan's policy or policies. The interactive aspects can, in some embodiments, use a graphical user interface in which custom-generated questions are presented to the user in order to determine, in an efficient and effective manner, and in a streamlined and user-friendly format, whether a particular product or service is covered by the policy. These and other functions can be performed through the use of decision-tree type interactions that are adapted and configured to employ particular "criteria." Based on the complexity of a particular policy, there may be hundreds or more possible permutations of the decision tree utilizing various policy-specific criteria to then yield an "outcome" to the end user, which can give a definitive indication on whether the particular condition and/or condition's related medical products or services are covered or not covered by a health plan's policy.

Figure 8:
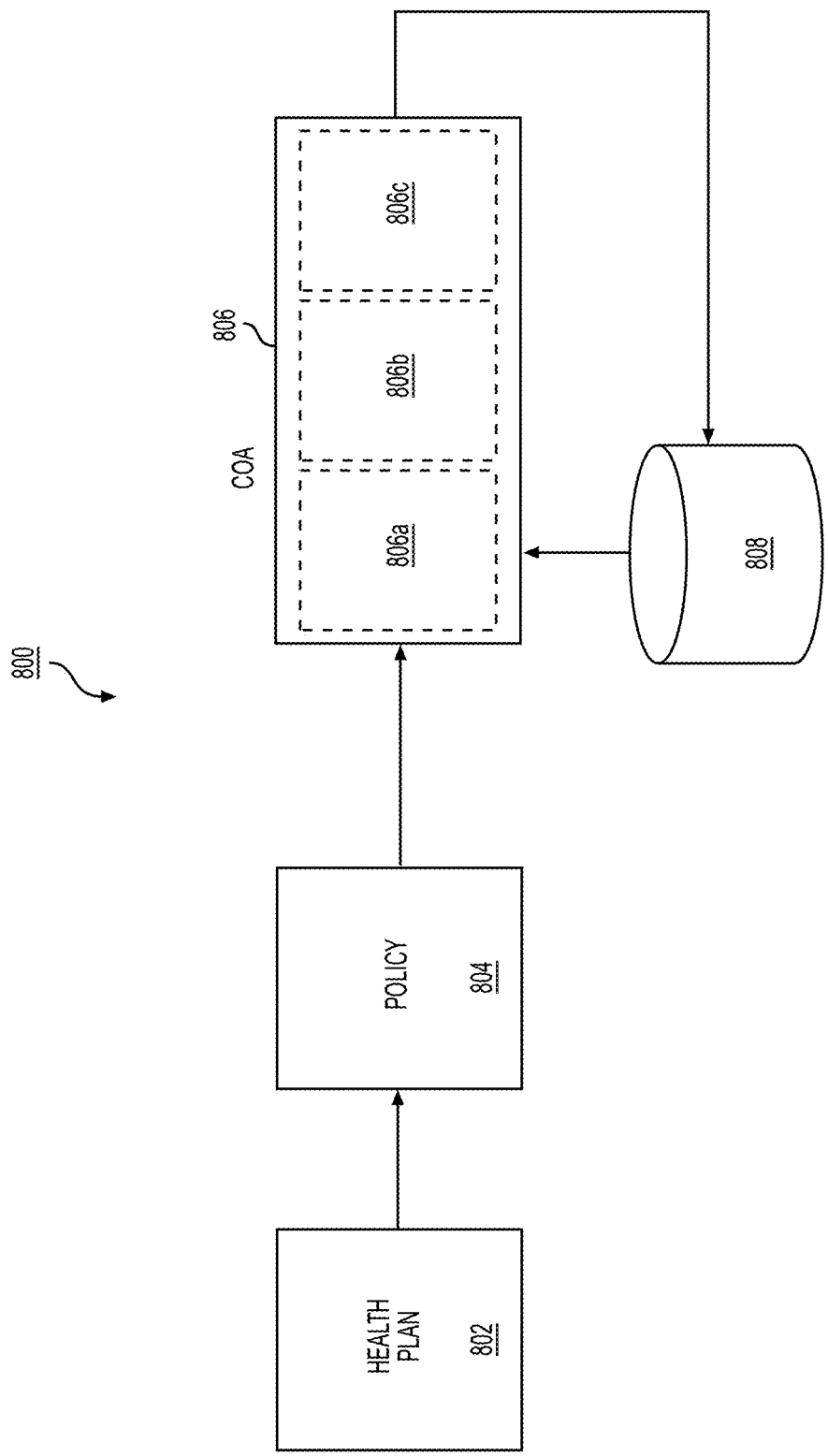
FIG. 8 is a diagram of a system and processes for performing certain aspects relating to health plan policies in accordance with some embodiments of the present disclosure.
Figure 10:
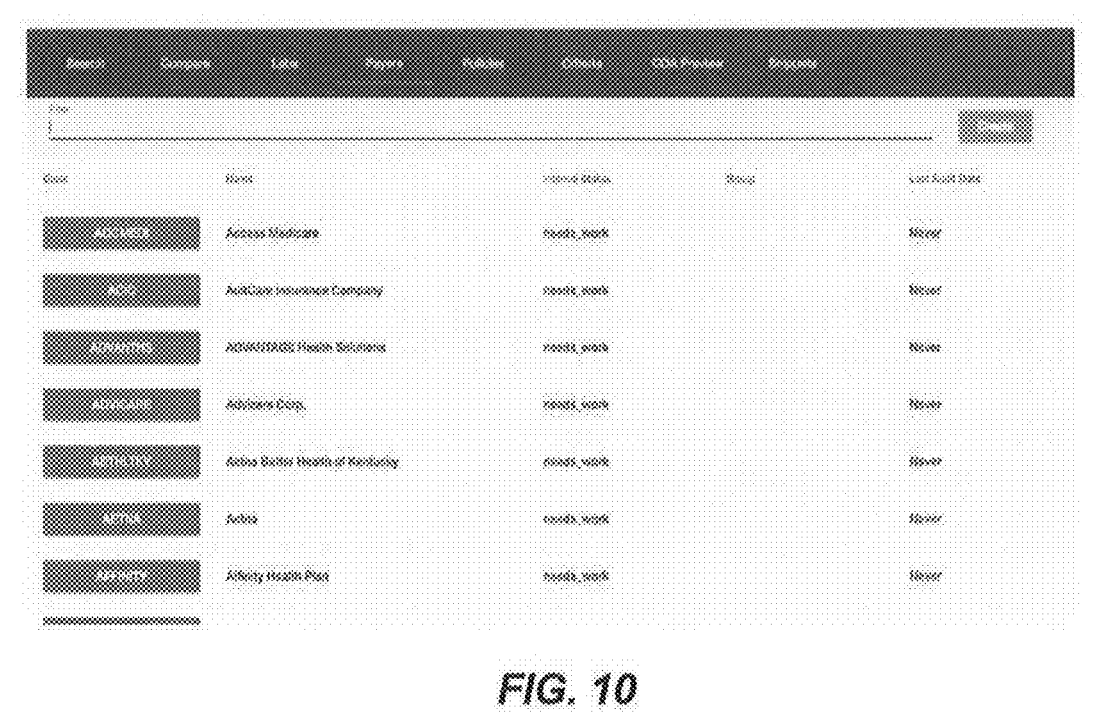
Figure 11:
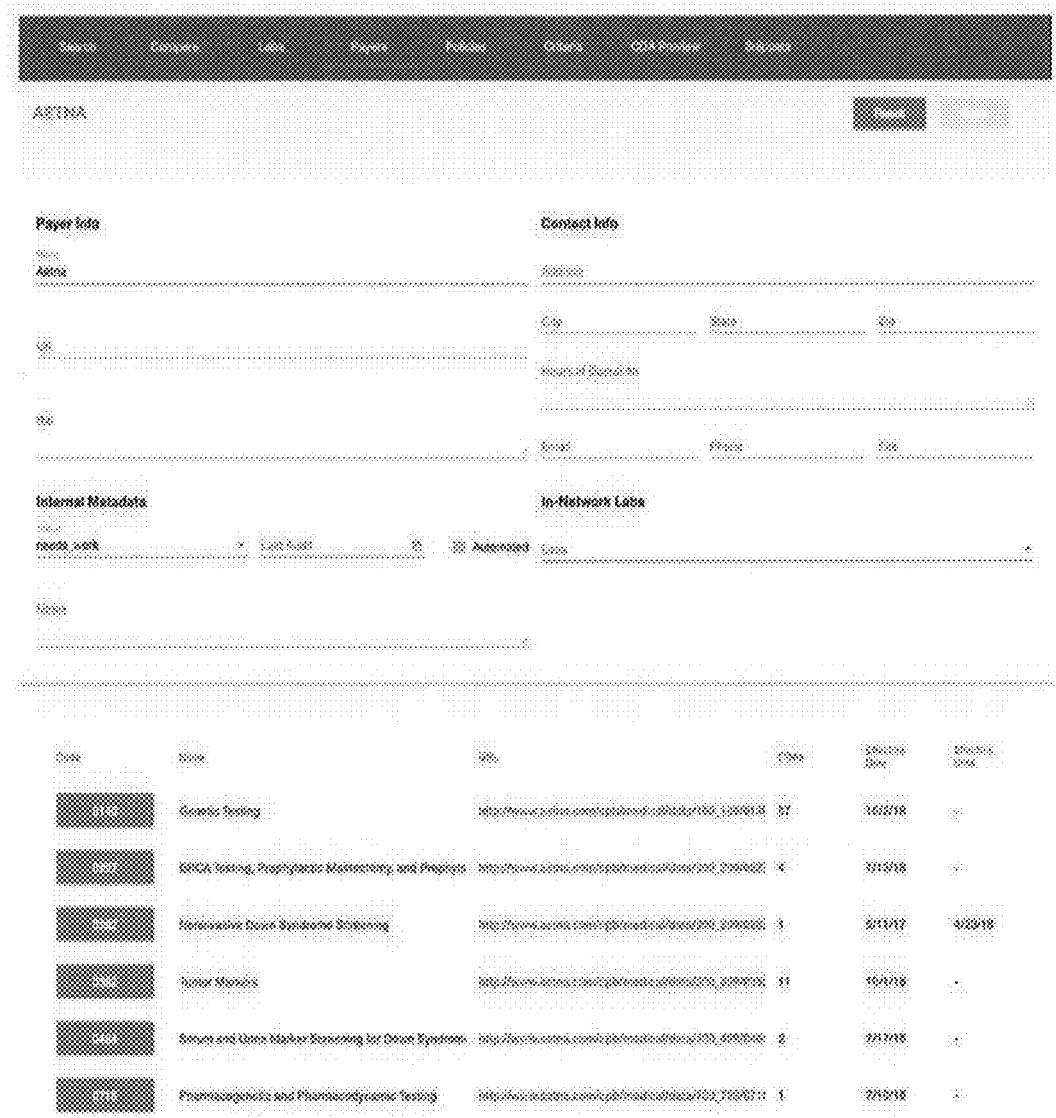

Now referring to the flow diagram of FIG. 8, first, data associated with a "Health Plan" 802 can be acquired from, for instance, websites or other publicly available sources where a health plan (e.g., health insurance provider) provides policy information associated with health-related testing products or services such as genetic-related tests products and services. FIG. 10 is a screenshot showing a graphical user interface display with a list of health plans that are being tracked and actively monitored and updated, in accordance with some embodiments, for policy-related information (corresponding to "Health Plan" 802 in the flow diagram of FIG. 8), and for which "curated" policies are available. The curation of a policy, and curated policy data structures, in accordance with some embodiments of the present disclosure, are described below in further detail. FIG. 11 shows, for a selected health plan (e.g., using the user interface shown in the screenshot of FIG. 10), specific corresponding policies. For example, as shown, FIG. 11 is a screenshot showing policies of a particular health plan, including codes assigned to the various tests, names, and a number of COAs for that policy; often there will be numerous COAs for each policy, particularly in lengthy or complex medical policies; often a policy may cover more than one test, or a wide range of testing such as whole areas of testing, under which there may be many types of tests and many different scenarios under which a patient may be considered by navigating decision tree(s) (based on criteria for a particular policy) to determine outcomes regarding coverage. FIG. 11 corresponds to the "Policy" block 804 in the flow diagram of FIG. 8.

Figure 12:
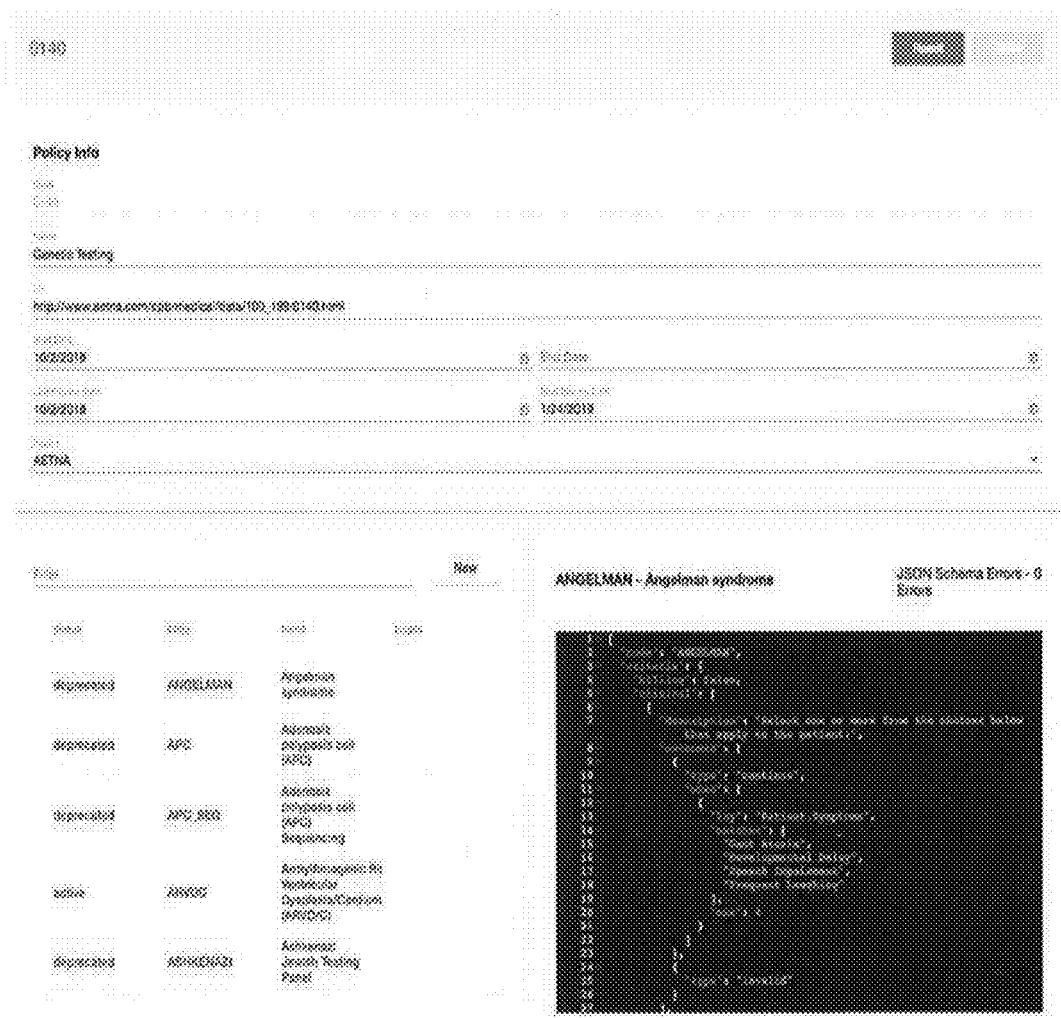
Figure 13:
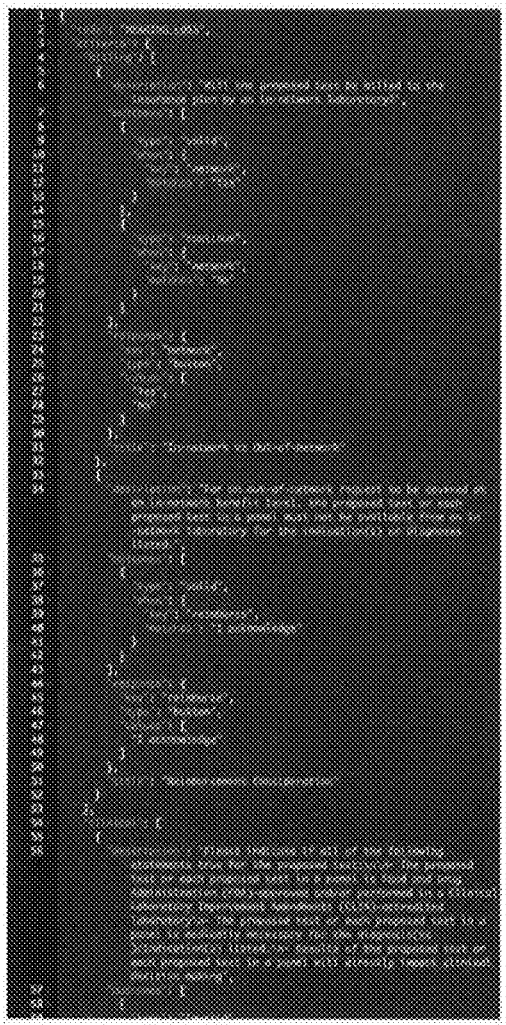

As mentioned briefly above, a health plan policy may be curated through a curation process to form a curated policy 804, in accordance with some embodiments. In accordance with various aspects of the present disclosure, coverage outcome algorithms (COAs) can include criteria for multiple different types of tests. The screen shot of FIG. 12 shows a list of COAs for a policy (this example corresponds to policy code 0140 from FIG. 11). The screen shot of FIG. 13 shows a data structure representation of a coverage outcome algorithm (COA) and presentation of the data. It should be recognized, therefore, that the screen shots of FIGS. 10-13 illustrate tools for a user that is involved in the "curation" of one or more particular policies, for example in the production to generate curated policy data to represent a particular policy's terms, and particularly its coverage and the associated required conditions that must be met. These tools may be designed by and utilized by, for example, a computer scientist or other party maintaining, building, and/or monitoring, etc. the tools that an end user such as a physician or health plan representative may ultimately use through other interfaces and tools for ordering tests and/or evaluating coverage by a policy, such as the through the embodiments of the system with the graphical user interface shown in the screen shots of FIGS. 14A-14F.

Referring again to FIG. 8, in some embodiments of the present disclosure a COA 806 is formed of three components: triggers 806*a*, criteria 806*b*, and outcomes 806*c*. Triggers 806*a* relate to the particular tests, including information on specificity of the tests and/or category of the test (e.g., Bin and/or GTU). The criteria 806*b* (discussed in further detail below) for a health plan and policy may apply broadly to a type of tests or a class of testing, or to a specific test from a specific laboratory, for instance. The "trigger" related information is used, for example, when a user places an order for a particular test (see also discussion below of "Test Orders" with respect to FIG. 9), such that a predetermined category results in a particular COA being utilized. Different triggers may, in some embodiments, be assigned to different parts of a policy. The criteria component 806*b* can be considered data that is representative of a questions and answers of a decision tree, further details of which are shown in the examples of FIGS. 14A-14F and the corresponding further description below. Each criteria question can have an associated key which defines a data field that would populate the answer to the criteria question. For instance, if the question is "Is the patient over the age of 40?", then the data field is "age" and the key may be "age >40". This functionality provides for the auto-population of answers to the questions from other clinical data sources (e.g., EHRs, LIMS systems, Member files).

FIGS. 14A-14F are screen shots of a user interface display by which a user can answer questions about a particular patient with respect to a particular condition the patient may have. These questions and their respective requested information are based on criteria-based questions, which can include, among other types of questions, questions regarding billing criteria, such as whether the genetic test will be billed to the particular healthcare plan (e.g., health insurance provider) through an in-network laboratory. The interactive elements for a user to answer the questions can include, but are not limited to, checkbox questions, questions with options from drop-down menus, or other multiple-choice type questions. According to these "criteria" aspects, in some embodiments, the answers provided by the user provide a sort of documentation and data that a patient must meet certain criteria, pertaining to what goes into the policy. For example, it may be that to get coverage under a certain policy, the patient must have one or more specific criteria met in a certain way in order to qualify for a certain test or type of testing for a potential condition. In this way, the language and requirements of a specific policy are effectively interpreted and structured.

Figures 14A, 14B:
Figures 14E, 14F:

Now specifically referring to the embodiments of the present disclosure shown in the screenshots of FIGS. 14A-14F, once a test is selected and insurance information is entered, by an "ordering provider" (e.g., user such as a medical professional or health plan representative), the ordering provider may be presented with a graphical display such as that shown in the example screen shot of FIG. 14A. Using the policy information, the ordering provider can see whether or not prior authorization is required and can use the "source" link to see the source from which the information comes. By selecting "Verify clinical criteria" in FIG. 14A, the ordering provider sees a first criterion, illustrated by FIG. 14B. After answering inquiries of the first criterion, the ordering provider then may see subsequent criterion, such as shown in the screenshot of FIG. 14C. As shown in FIG. 14D, once all of the questions are answered by the ordering provider, the ordering provider is presented with an outcome ("Criteria Met"). By selecting "clinical criteria outcome" via the interface shown in the screenshot of FIG. 14D, more detail can be seen, as shown in the screenshot of FIG. 14E. As shown in FIG. 14F, the ordering provider can also view any forms necessary for coverage of the test, by selecting "View documentation requirements." In various embodiments, an outcome can be considered the endpoint of a decision tree, after a user has navigated through each of the questions. Outcomes can be: "covered", "not covered", "indeterminate", or another indication (for example, an indication that further review by an expert would be required to make a determination on coverage).

Further aspects of the "Triggers" component 806a shown in FIG. 8 will now be described, in accordance with certain aspects and embodiments of the present disclosure. A trigger may be used, for example, when a user places an order for a particular test, to prompt a particular COA to determine which criteria to utilize in producing queries to a user. In effect, according to certain embodiments, the written medical policy from a health plan is curated into a data structure and then that data structure can be used to generate an interactive interface to guide the user through a decision tree, based on a policy's particular criteria, to produce the result of a coverage outcome. It should be noted that questions in the interactive process based on criteria for the policy can be particularly triggered in an automated way based on specific categories of tests. Accordingly, if an end user is ordering a test that happens to fall within a specific predetermined category (i.e., Bin) of tests, then that category can serve as a type of source to automate the prompting of the relevant questions to the end user. In some embodiments, for certain types of tests and/or Bins (categorizations) of tests, for example, it is the case for some policies that there is no coverage regardless of the circumstances, and these strict outcomes may be predetermined and, when applicable, provided to the user quickly without the need to navigate a lengthy decision tree. In some embodiments, a COA may have an associated (e.g., assigned) GTU, such that there may be one or more particular triggers for criteria that are based on a particular GTU, for instance in an implementation in which a health plan policy has specific criteria for very specific tests from a specific lab.

The triggers can correspond to one or more identifiers for the medical service or product. The identifiers can be, but are not limited to, the GTU or categorical Bin associated with a particular medical service or product. Further detail on GTUs and Bins is discussed above. Determining applicable identifier(s) for a medical service or product can be determined at least in part using machine learning. As such, machine learning may be utilized to determine the identifier to be associated with correct "triggers" for full implementation of the COAs to thereby produce a coverage outcome.

A model training client (e.g., 606 in FIG. 6) can be used to perform functions associated with model training in machine learning, according to some embodiments described herein, and for example functions for matching identifiers to a medical service or product. Alternatively, the machine learning may be performed automatically, i.e., unsupervised machine learning. In some embodiments, in order for an identifier to be determined (i.e., matched and/or attributed) for a medical product or service, a base model (see, e.g., model 610) may be used to make first "predictions" on a first set of data, for example a decision that a particular identifier corresponds to and should be matched to a particular medical product or service. In embodiments utilizing supervised machine learning, a user (see, e.g., user 602) such as an analyst may then correct incorrect results from the first predictions. The corrected data may then be used to train (see "training 608") to produce a new model (e.g., enhanced, improved, further trained model of model 610) based on the corrections made to the first data. This new model may then be used to make predictions on second data, and so on accordingly. This prediction, correction, and training process may progressively improve a model as additional items are processed. In some embodiments, one or more functions of the training, prediction, and feedback processes may be unsupervised, for example they may be performed autonomously by computer without user intervention.

In some embodiments, determining the identifier(s) for a particular product or service, such as to associate them with certain GTUs or Bins for downstream utilization with "triggers" and the other aspects described herein for implementing COAs to yield coverage outcomes, can be performed by using one or more machine learning algorithms, whereby a certain medical service or product selected (for example, ordered or evaluated by a user) is matched to one or more applicable GTUs and/or Bins based on a training dataset. This training dataset can be comprised of many medical services or products that may be appended to a GTU and/or Bin. In some embodiments, many supervised machine learning models take this training data and labels and learn weights or parameter values that, when applied to a new medical service or product, lead to the selection of the most likely GTU and/or Bin. Some examples of the models employed in some embodiments are XGBoost, Naïve Bayes, Support Vector Machines, Deep Learning using various architectures such as LSTM, and random forests.

Each machine learning algorithm can be considered and evaluated for best performance by using a portion of the training set to perform an ultimate inference task of GTU and Bin assignment and then checking the results against expert-applied labels. Then, in accordance with some embodiments, the best algorithm can be used to associate estimated identifier(s) with previously unidentified data. These data can then be evaluated for inclusion in the training dataset. In this way, the training dataset can grow in an iterative approach.

Figure 9:
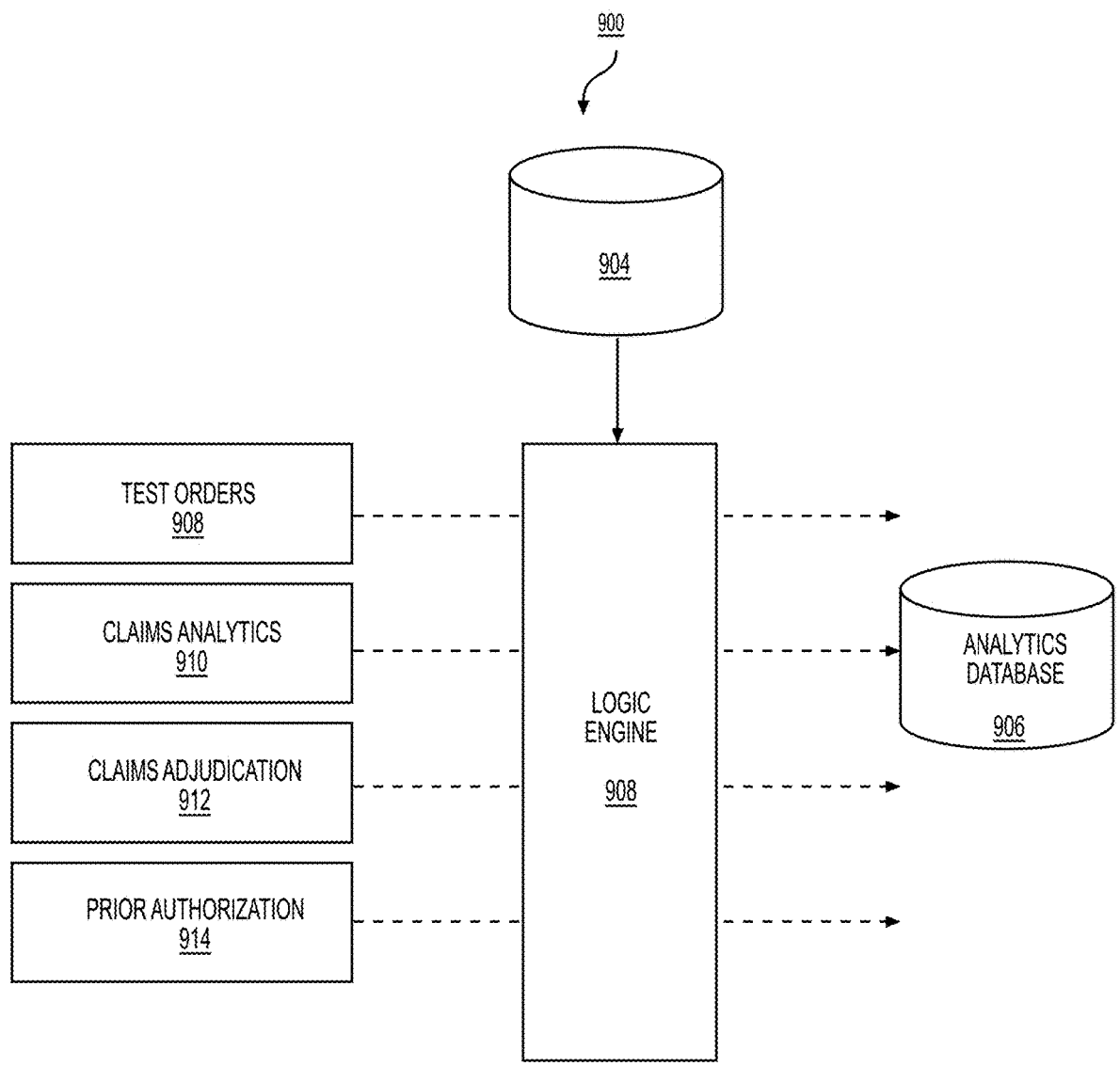
FIG. 9 is a diagram of a system and processes for performing further aspects relating to health plan policies in accordance with some embodiments of the present disclosure.

Referring again to FIG. 8, in some embodiments there can be an Expert Review (not shown), which may entail an expert analyst verifying whether any interpretations of the policy terms that were made during the curation process (e.g., a process generating a data structure representative of the health policy and/or a COA) were made correctly, e.g., that the interpretation is accurate to the written medical policy. The expert review in these embodiments may be similar to and have one or more functions as the expert review illustrated in and described with respect to the embodiment of FIG. 4. A generated, "curated" policy data structure can go from the expert review back into a database for storage (e.g., "Analytics Database" 906 shown in FIG. 9, which may be similar to and have one or more functions and/or components of the analytics database illustrated in and described with respect to the embodiments shown in FIG. 4), to be used in various particular applications described below. Alternatively, a curated policy data structure may go directly into the database without expert review, in some embodiments. The database may be part of, or be operatively associated with, a Squid 808, which may be similar to and have one or more functions and/or components of the squid illustrated in and described with respect to the embodiments shown in FIGS. 3A-3D. The squid 808 can serve as a central database for, among other data, Bins, GTUs, Labs, and COAs. As shown in FIG. 9 and as will be described in further detail below, the curated policy data structure (e.g., COA) can be utilized in a variety of applications (implementations) relating to: test orders; evaluating whether claims have been paid against a policy; claims adjudication; and/or prior authorization.

Now referring to the system and processes shown in FIG. 9 (collectively "900"), a logic engine 902 may be used for systematic applications of a policy for which there is a curated policy data structure. In some embodiments, the logic engine 902 and other components shown in FIG. 9, and any other functional components for performing their respective functions, can reside in executable program modules (e.g., program modules 714 in FIG. 7) or other software constructs, or in dedicated programmed hardware components. These and other functional components of the embodiments may be stored in memory devices (e.g., memory 704 or mass storage 712) and executable by processors (e.g., processing unit 702) of one or more computers, such as the computer 700 shown in FIG. 7. The Squid 904 and Analytics Database 906 can be implemented through one or more storage devices, such as in local electronic data storage devices (e.g., data store 716) or external electronic data storage devices such as remote databases.

The logic engine 902 can perform, among other functions, operations to navigate a user through a decision tree, for the user to input data and to arrive at an outcome. "Test Orders" 908 can refer to the process whereby a provider (e.g., physician for a particular patient) goes through criteria-based questions to determine if a medical product or service, such as a testing product or service, will be covered by a payer for a particular patient. As an example implementation, the provider (e.g., physician) selects a particular testing product or service, the specific test's identity in turn is the trigger for a COA curated for the specific patient's health insurance policy or plan, and the provider provides input to answer the criteria-based questions, to yield a determination as to whether the testing product or service is covered by the patient's insurance policy or plan. "Claims Analytics" 910 can refer to looking at a genetic testing claim (e.g., a claim for payment, i.e. payment/reimbursement/coverage for a particular ordered test) and then classifying that claim and putting it into a Bin (category), and once the claim has been classified into a Bin (which may have a respective Bin identifier), then some of the logic can be applied automatically; for example, for a certain subset of claims that are never covered, the outcome can be determined without human interaction. In some embodiments, additional clinical information (e.g., from an EHR) may be available with respect to a certain type of test or associated condition, for example a diagnosis code, and a system according to some embodiments can assemble those elements of the data structure to answer the questions for the user without any user interaction being required to arrive at an outcome. The implementation of "Claims Adjudication" 912, in some embodiments, can assist a health plan to determine whether or not to pay for a particular test, systematically, and/or recode or reprice according to a systematic logic. "Prior Authorization" 914 is similar to a test ordering process, but the user answering related questions is a different user than the user ordering a test. Rather than a provider going through all the criteria-based questions on the front end when ordering a test, in these embodiments, the user is, for example, a medical director and/or health plan representative evaluating particular criteria when he/she is doing a manual review on a claim that has been submitted.

Although some embodiments described herein have been described in language specific to computer structural features, methodological acts and by computer readable media, it is to be understood that the disclosure defined in the appended claims is not necessarily limited to the specific structures, acts or media described. Therefore, the specific structural features, acts and mediums are disclosed as exemplary embodiments implementing the claimed disclosure.

This written description uses examples to disclose certain implementations of the disclosed technology, including the best mode, and also to enable any person of ordinary skill to practice certain implementations of the disclosed technology, including making and using any devices or systems and performing any incorporated methods. The patentable scope of certain implementations of the disclosed technology is defined in the in the claims here appended and their equivalents, and may include other examples that occur to those of ordinary skill. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for determining whether a health policy covers a genetic testing service or product, comprising:
    receiving information that indicates a genetic testing service or product and a health policy that covers certain services or products;
    determining an identifier corresponding to the genetic testing service or product based on the received information, wherein the identifier comprises a genetic testing unit (GTU) for the genetic testing service or product,
        wherein the GTU is a consistent identifier for tracking a plurality of attributes of the genetic testing service or product over time, and
        wherein determining the identifier comprising the GTU comprises using a machine learning model to match the identifier to the genetic testing service or product based on a training dataset;
    associating the determined identifier corresponding to the genetic testing service or product with a corresponding coverage outcome algorithm (COA) from among a plurality of coverage outcome algorithms (COAs), wherein each COA has associated coverage criteria for determining a coverage outcome;
    prompting, through an interactive user interface, the user with specific queries for information associated with the genetic testing service or product and/or health plan policy, wherein the queries are based on the respective coverage criteria corresponding to the COA;
    receiving user responses to the queries through the interactive user interface;
    determining, based on the user responses, a coverage outcome indicating whether the health policy covers the genetic testing service or product; and
    outputting the coverage outcome to the user.

2. The method of claim 1, wherein the COAs utilize triggers associated with the genetic testing service or product.

3. The method of claim 1, wherein the identifier further comprises a categorical bin associated with the genetic testing service or product.

4. The method of claim 1, wherein the identifier correspond to a claim for coverage for the genetic testing service or product.

5. The method of claim 1, wherein at least some of the queries are customized according to the identity of the user as a patient, health care provider, or health policy representative.

6. The method of claim 2, further comprising:
based on at least one of the triggers, determining whether there is a predetermined coverage outcome corresponding to the genetic testing service or product; and
responsive to determining that there is a predetermined coverage outcome, outputting the predetermined coverage outcome to the user.

7. The method of claim 1, wherein the GTU's plurality of attributes of the genetic testing service or product tracked over time comprise one or more of: test code; target gene; time-to-results; and laboratory code.

8. A system, comprising:
one or more processors;
an interactive user interface;
a memory device coupled to the one or more processors and storing instructions that, when executed by the one or more processors, cause the system to perform functions for determining whether a health policy covers a genetic testing service or product, and wherein the performed functions comprise:
receiving information that indicates a genetic testing service or product and a health policy that covers certain services or products;
determining an identifier corresponding to the genetic testing service or product based on the received information, wherein the identifier comprises a genetic testing unit (GTU) for the genetic testing service or product,
wherein the GTU is a consistent identifier for tracking a plurality of attributes of the genetic testing service or product over time, and
wherein determining the identifier comprising the GTU comprises using a machine learning model to match the identifier to the genetic testing service or product based on a training dataset;
associating the determined identifier corresponding to the genetic testing service or product with a corresponding coverage outcome algorithm (COA) from among a plurality of coverage outcome algorithms (COAs), wherein each COA has associated coverage criteria for determining a coverage outcome;
prompting, through the interactive user interface, the user with specific queries for information associated with the genetic testing service or product and/or health plan policy, wherein the queries are based on the respective coverage criteria corresponding to the COA;
receiving user responses to the queries through the interactive user interface;
determining, based on the user responses, a coverage outcome indicating whether the health policy covers the genetic testing service or product; and
outputting the coverage outcome to the user.

9. The system of claim 8, wherein the COAs utilize triggers associated with the genetic testing service or product.

10. The system of claim 8, wherein the identifier further comprise a categorical bin associated with the genetic testing service or product.

11. The system of claim 8, wherein the identifier correspond to a claim for coverage for the genetic testing service or product.

12. The system of claim 8, wherein at least some of the queries are customized according to the identity of the user as a patient, health care provider, or health policy representative.

13. The system of claim 9, wherein the memory device stores further instructions that, when executed by the one or more processors, cause the system to:
determine, based on at least one of the triggers, whether there is a predetermined coverage outcome corresponding to the genetic testing service or product; and
responsive to determining that there is a predetermined coverage outcome, outputting the predetermined coverage outcome to the user.

14. A non-transitory computer-readable medium storing instructions that, when executed by one or more processors, cause one or more computing devices to perform functions for determining whether a health policy covers a genetic testing service or product, and wherein the performed functions comprise:
receiving information that indicates a genetic testing service or product and a health policy that covers certain services or products;
determining an identifier corresponding to the genetic testing service or product based on the received information, wherein the identifier comprises a genetic testing unit (GTU) for the genetic testing service or product,
wherein the GTU is a consistent identifier for tracking a plurality of attributes of the genetic testing service or product over time, and
wherein determining the identifier comprising the GTU comprises using a machine learning model to match the identifier to the genetic testing service or product based on a training dataset;
associating the determined identifier corresponding to the genetic testing service or product with a corresponding coverage outcome algorithm (COA) from among a plurality of coverage outcome algorithms (COAs), wherein each COA has associated coverage criteria for determining a coverage outcome;
prompting, through an interactive user interface, the user with specific queries for information associated with the genetic testing service or product and/or health plan policy, wherein the queries are based on the respective coverage criteria corresponding to the COA;
receiving user responses to the queries through the interactive user interface;
determining, based on the user responses, a coverage outcome indicating whether the health policy covers the genetic testing service or product; and
outputting the coverage outcome to the user.

15. The computer-readable medium of claim 14, wherein the COAs utilize triggers associated with the genetic testing service or product.

16. The computer-readable medium of claim 14, wherein the identifier further comprises a categorical bin associated with the genetic testing service or product.

17. The computer-readable medium of claim 14, wherein the identifier corresponds to a claim for coverage for the genetic testing service or product.

18. The computer-readable medium of claim 14, wherein at least some of the queries are customized according to the identity of the user as a patient, health care provider, or health policy representative.

19. The computer-readable medium of claim 15, further comprising:
  based on at least one of the triggers, determining whether there is a predetermined coverage outcome corresponding to the genetic testing service or product; and
  responsive to determining that there is a predetermined coverage outcome, outputting the predetermined coverage outcome to the user.

20. The computer-readable medium of claim 14, wherein the GTU's plurality of attributes of the genetic testing service or product tracked over time comprise one or more of: test code; target gene; time-to-results; and laboratory code.

\* \* \* \* \*